(12) United States Patent
Wigginton et al.

(10) Patent No.: US 12,016,593 B2
(45) Date of Patent: **\*Jun. 25, 2024**

(54) EXTERNAL FIXATION FOR THE CORRECTION OF BONE DEFORMITY AND TRAUMA

(71) Applicant: New Standard Device, LLC, San Antonio, TX (US)

(72) Inventors: Robert E. Wigginton, McKinney, TX (US); Bryant T. Phamvu, San Antonio, TX (US); Adam P. Shonebarger, San Antonio, TX (US); C. Douglas Klein, Jr., Andover, MA (US)

(73) Assignee: New Standard Device, LLC, San Antonio, TX (US)

( * ) Notice: Subject to any disclaimer, the term of this patent is extended or adjusted under 35 U.S.C. 154(b) by 281 days.

This patent is subject to a terminal disclaimer.

(21) Appl. No.: 17/687,945

(22) Filed: Mar. 7, 2022

(65) Prior Publication Data

US 2022/0257285 A1 Aug. 18, 2022

Related U.S. Application Data

(63) Continuation of application No. 17/236,040, filed on Apr. 21, 2021, now Pat. No. 11,266,445, which is a
(Continued)

(51) Int. Cl.
*A61B 17/64* (2006.01)
*A61B 17/62* (2006.01)
(Continued)

(52) U.S. Cl.
CPC .......... *A61B 17/6433* (2013.01); *A61B 17/62* (2013.01); *A61B 2017/00477* (2013.01);
(Continued)

(58) Field of Classification Search
CPC ......... A61B 17/60; A61B 17/62; A61B 17/64; A61B 17/6416; A61B 17/6425;
(Continued)

(56) References Cited

U.S. PATENT DOCUMENTS

| 5,062,844 | A | | 11/1991 | Jamison et al. |
| 5,540,686 | A | * | 7/1996 | Zippel ................ A61B 17/6441 606/56 |

(Continued)

OTHER PUBLICATIONS

Wikipedia; "Ilizarov apparatus"; dwonloaded from <https://en.wikipedia.org/wiki/Ilizarov_apparatus> on Apr. 22, 2019; last edited on Oct. 16, 2018.

*Primary Examiner* — Eduardo C Robert
*Assistant Examiner* — Christina Negrellirodriguez
(74) *Attorney, Agent, or Firm* — Gregory K. Goshorn; GREG GOSHORN, P.C.

(57) ABSTRACT

Provided is an apparatus and component parts of a system for the external fixation of bones. The component parts include fixation plates such as a C-shaped Plate, an N-shaped Plate, a J-shaped Plate, a K-shaped Plate, an I-shaped Plate, a Foor Plate, a Z-shaped Plate and a T-shaped Plate. Two or more fixation plates are configured along an axis, the two or more fixation plates; a plurality of telescoping adjustable struts that connect a first fixation plate along the axis with a second fixation plate of the plurality of fixation plates along the axis, wherein the first and second fixation plates are adjacent plates along the axis; and a plurality of posts, each post connecting two adjacent fixation plates of the plurality of fixation plates along the axis.

19 Claims, 21 Drawing Sheets

Related U.S. Application Data continuation-in-part of application No. 16/564,023, filed on Sep. 9, 2019, now Pat. No. 11,304,727, which is a continuation of application No. 15/922,577, filed on Mar. 15, 2018, now Pat. No. 10,413,328.

(51) Int. Cl.
*A61B 17/00* (2006.01)
*A61B 17/56* (2006.01)

(52) U.S. Cl.
CPC ............... *A61B 2017/00991* (2013.01); *A61B 2017/568* (2013.01)

(58) Field of Classification Search
CPC .............. A61B 17/6441; A61B 17/645; A61B 17/6458; A61B 17/6466
USPC .................................................... 606/56–59
See application file for complete search history.

(56) References Cited

U.S. PATENT DOCUMENTS

| | | | |
|---|---|---|---|
| 5,968,043 A | 10/1999 | Ross, Jr. et al. | |
| 8,574,232 B1 | 11/2013 | Ross et al. | |
| 10,413,328 B1 * | 9/2019 | Klein, Jr. | ............... A61B 17/62 |
| 2010/0234844 A1 | 9/2010 | Edelhauser et al. | |
| 2011/0118738 A1 | 5/2011 | Vasta et al. | |
| 2012/0143190 A1 | 6/2012 | Wolfson | |

* cited by examiner

EXTERNAL FIXATION FOR THE CORRECTION OF BONE DEFORMITY AND TRAUMA

CROSS-REFERENCES TO RELATED APPLICATIONS

The present application is a Continuation and claims the benefit of the filing date of an application entitled:

"External Fixation for the Correction of Bone Deformity and Trauma," Ser. No. 17/236,040, filed Apr. 21, 2021, now U.S. Pat. No. 11,266,445, issued Mar. 8, 2022, assigned to the assignee of the present application, and herein incorporated by reference, which is a Continuation-in-part and claims the benefit of the filing date of an application entitled:

"External Fixation for the Correction of Bone Deformity and Trauma," Ser. No. 16/564,023, filed Sep. 9, 2019, assigned to the assignee of the present application, and herein incorporated by reference, which is a Continuation and claims the benefit of the filing date of an application entitled:

"External Fixation for the Correction of Bone Deformity and Trauma," Ser. No. 15/922,577, filed Mar. 15, 2018, now U.S. Pat. No. 10,413,328, issued Sep. 17, 2019, assigned to the assignee of the present application, and herein incorporated by reference.

FIELD OF DISCLOSURE

The claimed subject matter relates to an external bone fixation system for the treatment of bone deformity and trauma.

BACKGROUND OF THE INVENTION

Current External Bone Fixation (EBF) systems for the treatment of bone deformity and acute trauma employ circular rings that surround a patient's limb. Typically, the diameter of such rings must be approximately four centimeters (4 cm) larger than the limb being treated to allow for swelling in the limb. Oversized rings to accommodate large extremities may also be used. Current systems are both uncomfortable for the patient and inconvenient when a wound is cleaned. One well-known reconstructive system is the Ilizarov frame, as shown in U.S. Pat. Nos. 4,365,624; 4,615,338; 4,978,348; 5,702,389 and 5,971,984. The Ilizarov frame uses a combination of circular frames, pins and wires for deformity correction. In addition, current Ern' systems for acute trauma may only provide a temporary fix until a definitive treatment is determined and they are unstable, difficult to move into a new position and have minimal or no weight bearing capability.

SUMMARY

Provided is a system for the external fixation of a bone in conjunction with the treatment of bone deformity and trauma. The system is applicable in, but not limited to, both adult and pediatric situations. The system includes a number of fixation plates such as a "C Plate," a "N Plate," a "J Plate," a "K Plate," an "I Plate," a "Foot Plate," a "Z Plate" and a "T Plate," which may be arranged in a variety of "single," "stacked," or "cascade" configurations. The C Plate may be employed to conform to the leg, hip and arm; the N Plate to a leg, arm and foot; the J Plate to the hip and leg; the K Plate to the pelvis and the Foot Plate to the foot. An I Plate may be employed to conform to a patient's foot or to extend portions of the other plates. The T Plate and Z Plate that may be used in conjunction with the other components.

Fixation plates are coupled with either posts, rods or telescoping struts and may include bridges to provide strength and stability. The disclosed technology enables ring-like fixation with stable point of fixation while leaving a posterior opening to allow for edema and easier access to the limb under treatment. Different plates may be selected by a Health Care Provider (HCP) so that the HCP is able to customize an external fixation device specifically for a particular patient's anatomy and the patients' treatment. The customized external fixation device is typically attached to a patient's extremity or pelvis by means of a combination of fixation devices such as, but not limited to, wires and pins.

Provided is an apparatus and component parts of a system for the external fixation of bones. The component parts include fixation plates such as a C Plate, a N Plate, a J Plate an I Plate, a K Plate, a Foot Plate, a Z Plate and a T Plate. The system includes a plurality of two or more fixation plates configured along an axis, the two or more fixation plates selected from a list, the list comprising a plurality of C Plates; a plurality of N Plates; a plurality of J Plates; a plurality of I Plates; a plurality of Z Plates, a plurality of T Plates, a plurality of telescoping adjustable struts that connect a first fixation plate of the plurality of fixation plates along the axis with a second fixation plate of the plurality of fixation plates along the axis, wherein the first and second fixation plates are adjacent plates along the axis; and a plurality of posts, each post connecting two adjacent fixation plates of the plurality of fixation plates along the axis.

This summary is not intended as a comprehensive description of the claimed subject matter but, rather, is intended to provide a brief overview of some of the functionality associated therewith. Other systems, methods, functionality, features, and advantages of the claimed subject matter will be or will become apparent to one with skill in the art upon examination of the following figures and detailed description.

BRIEF DESCRIPTION OF THE DRAWINGS

A better understanding of the claimed subject matter can be obtained when the following detailed description of the disclosed embodiments is considered in conjunction with the following figures.

DETAILED DESCRIPTION

The illustrations and diagrams in the Figures illustrate the architecture, functionality, and operation of possible implementations of systems according to various embodiments of the present invention.

Figure 1:
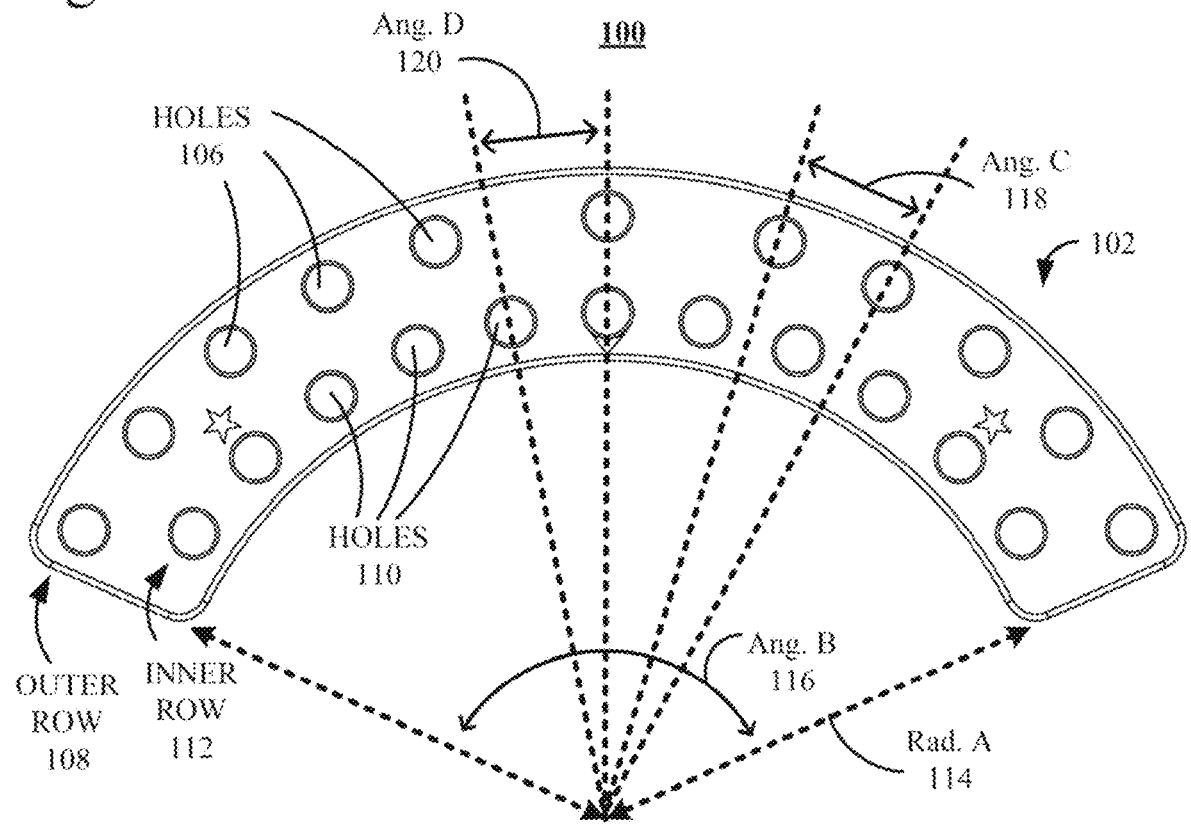
FIG. 1 is an illustration of one embodiment of a C Plate that may be employed in the claimed subject matter.
Figure 1:
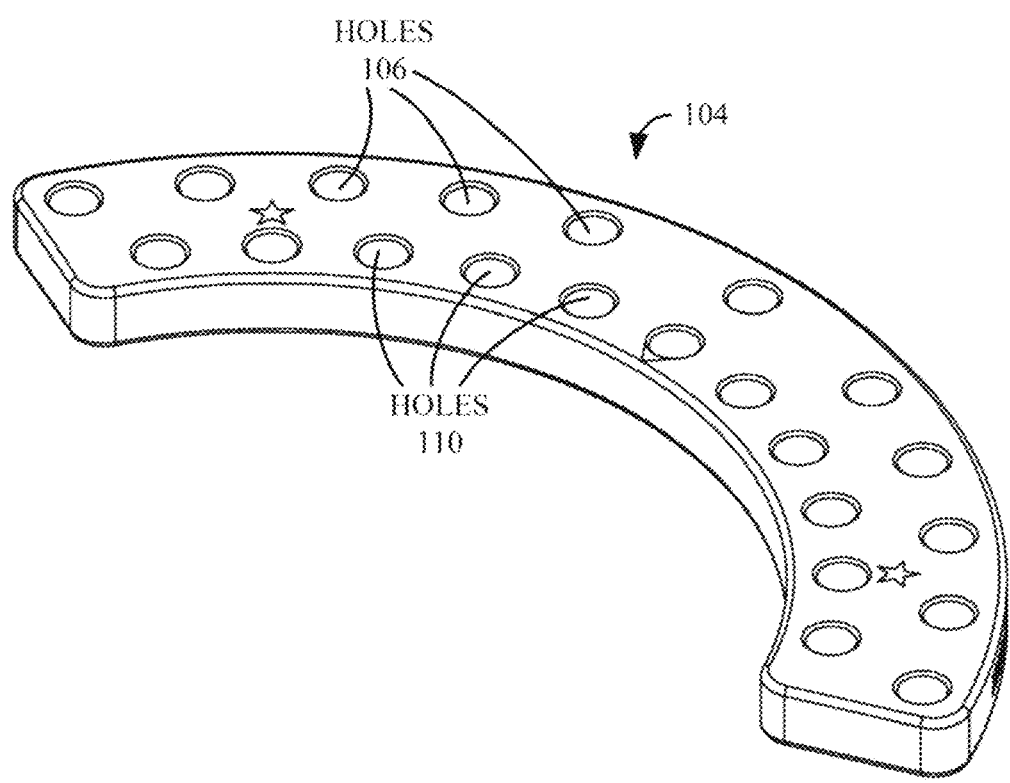

FIG. 1 is an illustration of two views of one embodiment of that which the Inventors have defined as a C Plate 100. C Plate 100 is illustrated from two (2) different angles, i.e., a top view 102 and a perspective view 104. C Plate 100 is typically employed to conform to a patient's extremity, or limb.

C Plate 100 has a semi-circular curvature that may follow the arc of a circle. C Plate 100 includes a row of holes 106, i.e. forming an outer row 108, and a row of holes 110, i.e., forming an inner row 112. For the sake of simplicity, only three holes in each of rows 108 and 112 are labeled. Rows 108 and 112 follow the curvature of C Plate 100. In this example, C Plate 100 covers an angle, or an Angle (Ang.) B 116, equal to approximately one hundred thirty-eight degrees (138°), although Ang. B 116 may be any angle greater than ninety degrees (90°) and less than one hundred eighty degrees (180°). For example, C Plate 100 may be available in '⅓' (120°), '⅝' (225°) and '¾' (270°) configurations. FIG. 1 corresponds to a C Plate #2 (See TAB. 1) in which a Radius (Rad.) A 114 corresponding to an interior radius of C Plate 100 is equal to seventy millimeters (70 mm), an Ang. C 148 is equal to an angle of eleven point two five degrees (11.25°) and an Ang. D. 120 is equal to an angle of eleven point two five degrees (11.25°).

TABLE 1 provides some examples of various sizes of C Plate 100 along with possible number and spacing, or angles, of holes in rows 108 and 112:

TABLE 1

| C Plate # | Rad. "A" In mm (114) | No. Outer Holes (106) | No. Inner Holes (110) | Angle "B" (116) | Angle "C" (118) | Angle "D" (150) |
|---|---|---|---|---|---|---|
| 1 | 60 | 10 | 9 | 133° | 12.86° | 12.86° |
| 2 | 70 | 12 | 11 | 133° | 11.25° | 11.25° |
| 3 | 80 | 14 | 13 | 138.2° | 10.00° | 10.00° |
| 4 | 90 | 16 | 15 | 142.6° | 9.00° | 9.00° |
| 5 | 100 | 16 | 15 | 133° | 8.18° | 8.18° |

Figure 2:
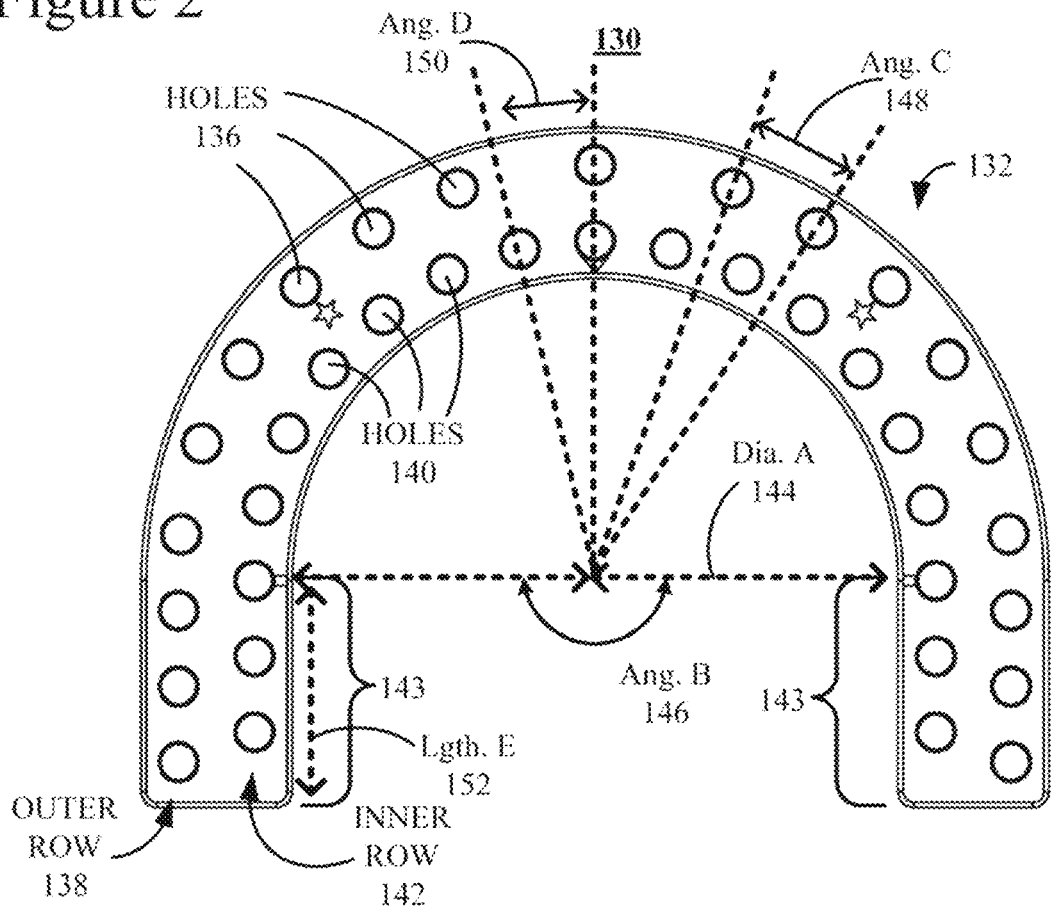
FIG. 2 is an illustration of one embodiment of an N Plate that may be employed in conjunction with the claimed subject matter.
Figure 2:
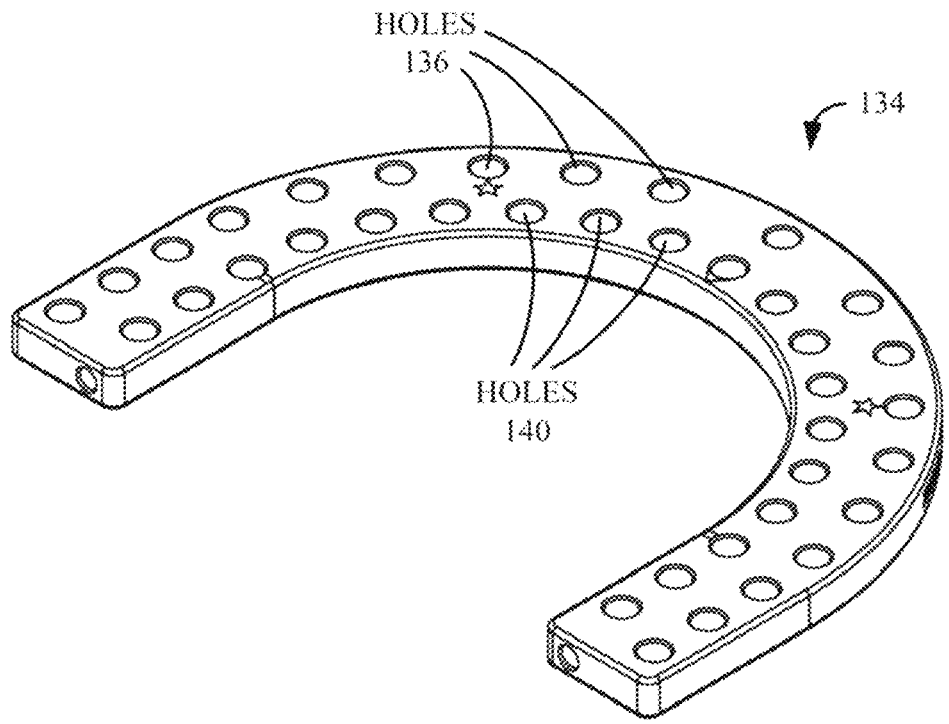

FIG. 2 is an illustration of two views of one embodiment of that which the Inventors have defined as an N Plate 130. N Plate 130 is illustrated from two (2) different angles, i.e., a top view 132 and a perspective view 134. N Plate 130 is typically employed to conform to a patients' extremity.

N Plate 130 includes a row of holes 136, i.e. forming an outer row 138, and a row of holes 140, i.e., forming an inner row 142. Rows 138 and 142 follow the curvature of N Plate 130 and extend into extensions 143 at the end of curvature. For the sake of simplicity, only three holes in each of rows 138 and 142 are labeled. Like C Plate 100, N plate 130 has a portion with a partial semi-circular curvature that may follow the arc of a circle. N Plate 130 also has straight extensions 143 at the ends of the curved portion. Straight extensions 143 are typically parallel to each other. In this example, the curved portion of N Plate 130 covers an Angle (Ang.) B 146, equal to approximately one hundred eighty degrees (180°). In alternative embodiments Ang. B 146 may also exceed 180°. FIG. 2 corresponds to an N Plate #2 (See TAB. 2) in which a Diameter (Dia.) A 144 corresponding to the interior diameter of N Plate 130 is equal to one hundred forty millimeters (140 mm), an Ang. C 148 is equal to an angle of eleven point two five degrees (11.25°), an Ang. D 150 is equal to an angle of eleven point two five degrees (11.25°) and the length of extensions 143, or a Lgth. E 148, is equal to sixty millimeters (60 mm).

TABLE 2 provides some examples of various sizes of N Plate 130 along with possible number and spacing, or angles, of holes in rows 138 and 142:

TABLE 2

| N Plate # | Dia. "A" In mm (144) | No. Outer Holes (138) | No. Inner Holes (142) | Angle "B" (146) | Angle "C" (148) | Angle "D" (150) | Lgth. "E" In mm (152) |
|---|---|---|---|---|---|---|---|
| 1 | 120 | 19 | 19 | 180° | 12.86° | 12.86° | 45 |
| 2 | 140 | 23 | 23 | 180° | 11.25° | 11.25° | 60 |
| 3 | 160 | 25 | 25 | 180° | 10.00° | 10.00° | 60 |
| 4 | 180 | 27 | 27 | 180° | 9.00° | 9.00° | 60 |

TABLE 2-continued

| N Plate # | Dia. "A" In mm (144) | No. Outer Holes (138) | No. Inner Holes (142) | Angle "B" (146) | Angle "C" (148) | Angle "D" (150) | Lgth. "E" In mm (152) |
|---|---|---|---|---|---|---|---|
| 5 | 200 | 29 | 29 | 180° | 8.18° | 8.18° | 60 |
| 6 | 240 | 31 | 31 | 180° | 7.50° | 7.50° | 60 |

Figure 3:
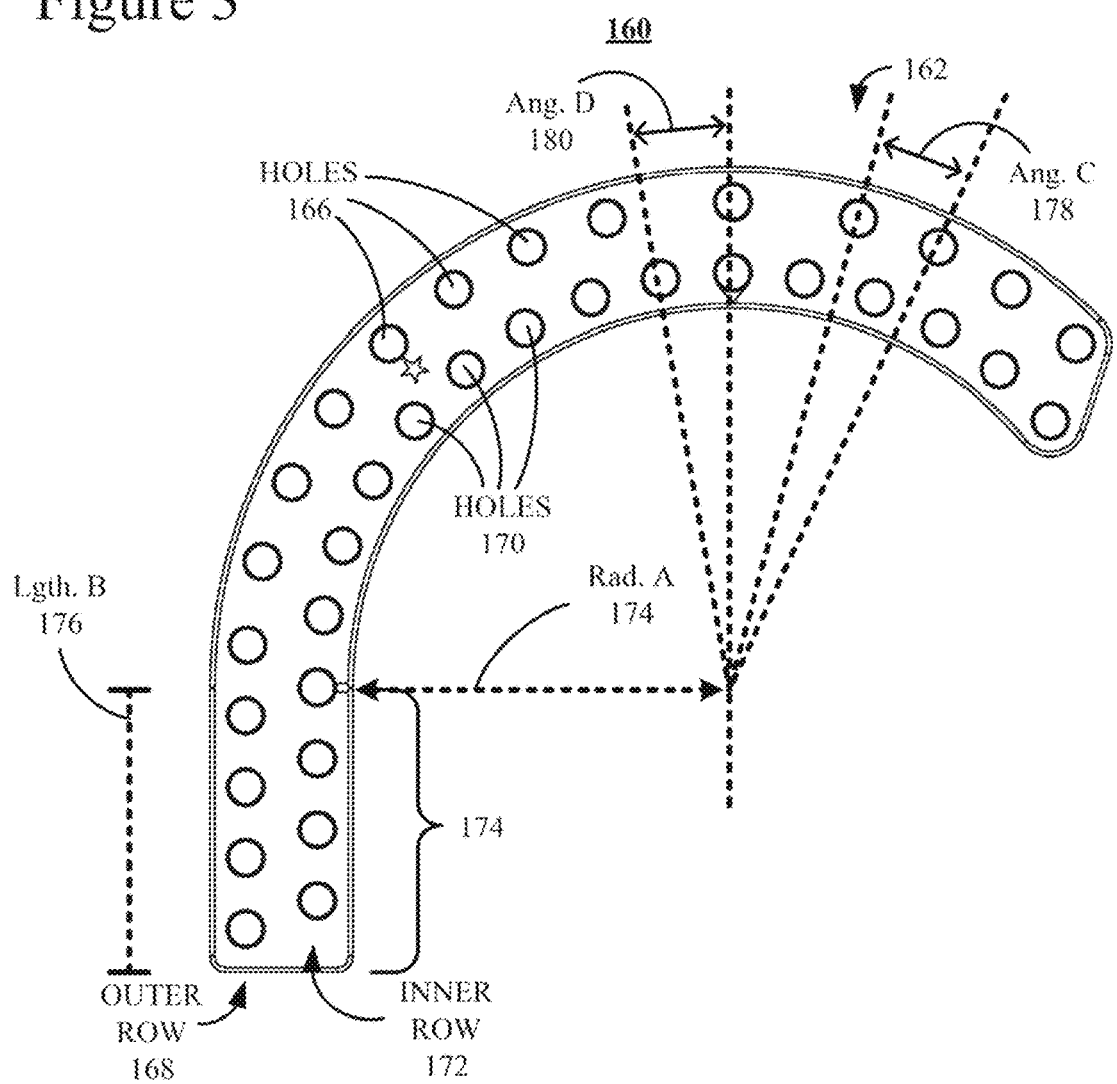
FIG. 3 is an illustration of one embodiment of a J Plate that may be employed in conjunction with the claimed subject matter.
Figure 3:
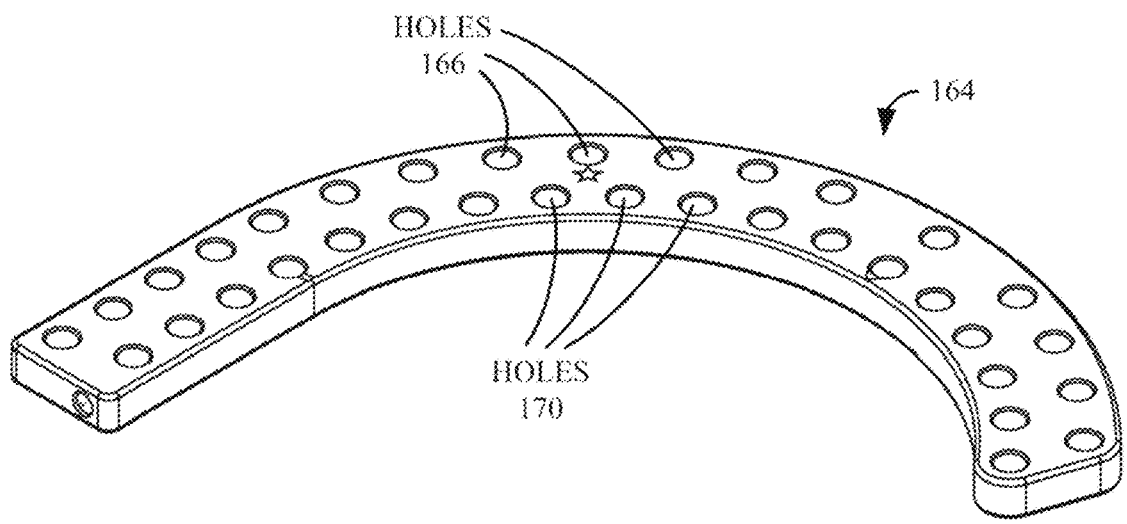

FIG. 3 is an illustration of two views of one embodiment of that which the Inventors have defined as an J Plate 160. J Plate 160 is illustrated from two (2) different angles, i.e., a top view 162 and a perspective view 164. J Plate 160 is typically employed to conform to a patient's extremity.

J Plate 160 includes a row of holes 166, i.e. forming an outer row 168, and a row of holes 170, i.e., forming an inner row 172. For the sake of simplicity, only three holes in each of rows 168 and 172 are labeled. Like C Plate 100, J plate 160 has a portion with a partial circular curvature that may follow the arc of a circle. J Plate also has a straight extension 174 at the one end of the curved portion. In this example, the curvature portion of J Plate 160 covers an angle equal to approximately one hundred thirty-eight degrees (140°), although the angle may be any angle greater than ninety degrees (90°) and less than one hundred eighty degrees (180°).

FIG. 3 corresponds to an J Plate #2 (See TAB. 3) in which a Radius (Rad.) A 174 corresponding to the interior radius of J Plate 160 is equal to seventy millimeters (70 mm), Angle (Ang.) C 178 is equal to an angle of eleven point two five degrees (11.25°), an Ang. D 180 is equal to an angle of eleven point two five degrees (11.25°) and the length of extension 176, or a Length (Lgth.) B 176, is equal to sixty millimeters (60 mm).

TABLE 3 provides some examples of various sizes of J Plate 160 along with possible number and spacing, or angles, of holes in rows 168 and 172:

TABLE 3

| J Plate # | Rad. "A" In mm (174) | No. Outer Holes (168) | No. Inner Holes (172) | Lgth. "B" In mm (176) | Ang. "C" (178) | Ang. "D" (180) |
|---|---|---|---|---|---|---|
| 1 | 60 | 13 | 13 | 45 | 12.86° | 12.86° |
| 2 | 70 | 16 | 16 | 60 | 11.25° | 11.25° |
| 3 | 80 | 18 | 18 | 60 | 10.00° | 10.00° |
| 4 | 90 | 19 | 19 | 60 | 9.00° | 9.00° |
| 5 | 100 | 20 | 20 | 60 | 8.18° | 8.18° |

Figure 4:
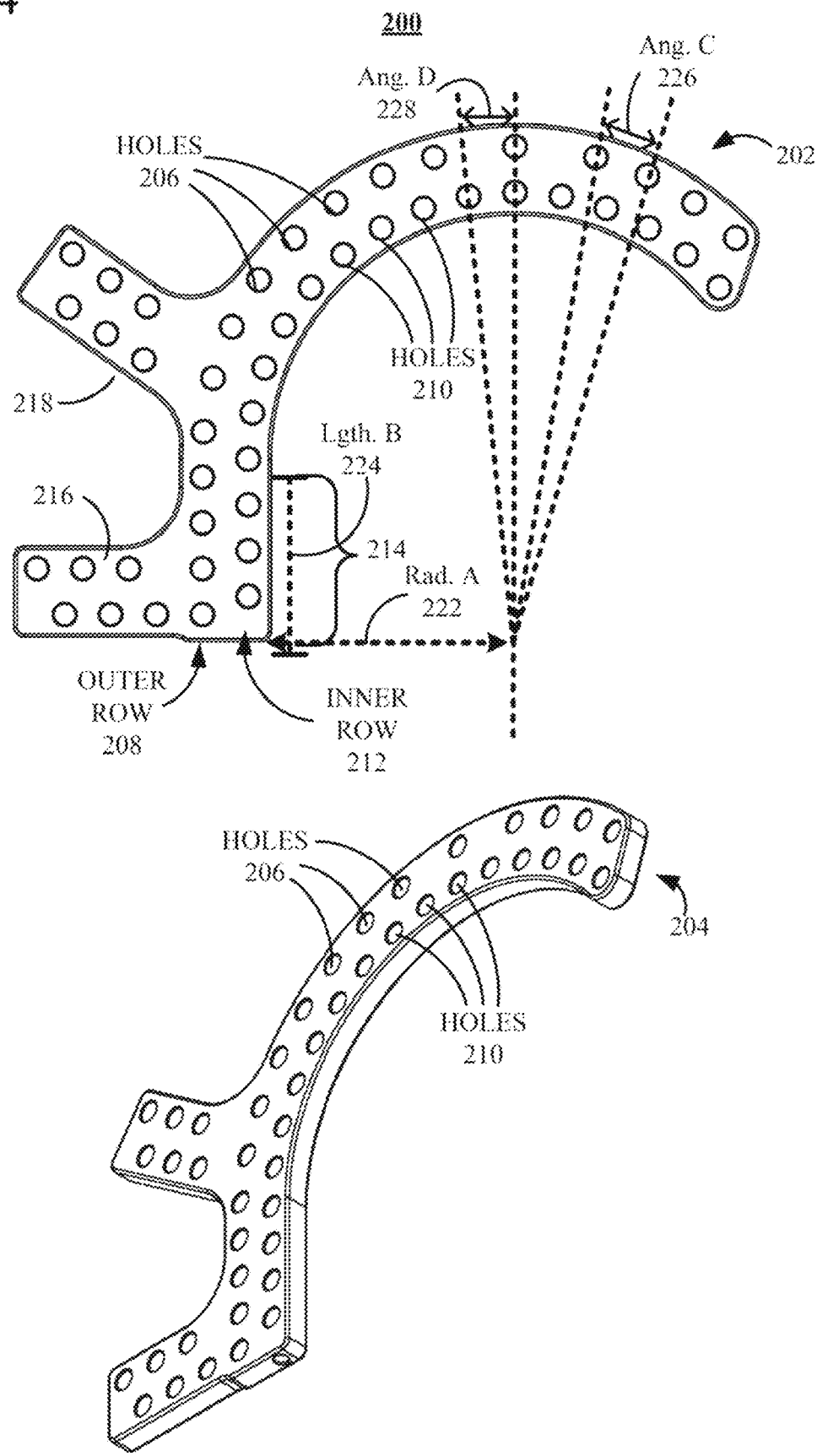
FIG. 4 is an illustration of one embodiment of a K Plate that may be employed in conjunction with the claimed subject matter.

FIG. 4 is an illustration of two views of one embodiment of that which the Inventors have defined as K Plate 200. K Plate 200 is illustrated from two (2) different angles, i.e., a top view 202 and a perspective view 204. K Plate 200 is typically employed to conform to a patient's pelvis.

K Plate 200 includes a row of holes 206, i.e. forming an outer row 208, and a row of holes 210, i.e., forming an inner row 212. For the sake of simplicity, only three holes in each of rows 208 and 212 are labeled. Like J Plate 160 (FIG. 1), K Plate 200 has a portion with a partial circular curvature that may follow the arc of a circle and a straight extension 214 at the one end of the curved portion. Unlike J Plate 160, in this example, K plate also has a straight extension 216 that extends from extension 214 and an extension 218, both of which extend outward from the side of the convex curved portion of K Plate 200. Alternative embodiments may only one or additional extensions such as extensions 214 and 216.

In this example, the curvature portion of K Plate 200 covers an angle equal to approximately one hundred forty degrees (140°), although the angle may be any angle greater than ninety degrees (90°) and less than one hundred eighty degrees (180°).

FIG. 4 corresponds to an K Plate #2 (See TAB. 4) in which a Radius (Rad.) A 222 corresponding to the interior radius of K Plate 200 is equal to seventy millimeters (70 mm), Angle (Ang.) C 226 is equal to an angle of eleven point two five degrees (11.25°), an Ang. D 228 is equal to an angle of eleven point two five degrees (11.25°) and the length of extension 214, or a Length (Lgth.) B 224, is equal to sixty millimeters (60 mm).

TABLE 4 provides some examples of various sizes of K Plate 200 along with possible number and spacing, or angles, of holes in rows 208 and 212:

TABLE 4

| K Plate # | Rad. "A" In mm (222) | No. Outer Holes (208) | No. Inner Holes (212) | Lgth. "B" In mm (224) | Angle "C" (226) | Angle "D" (228) |
|---|---|---|---|---|---|---|
| 1 | 60 | 13 | 13 | 45 | 12.86° | 12.86° |
| 2 | 70 | 16 | 16 | 60 | 11.25° | 11.25° |
| 3 | 80 | 18 | 18 | 60 | 10.00° | 10.00° |
| 4 | 90 | 19 | 19 | 60 | 9.00° | 9.00° |
| 5 | 100 | 20 | 20 | 60 | 8.18° | 8.18° |

Figure 5:
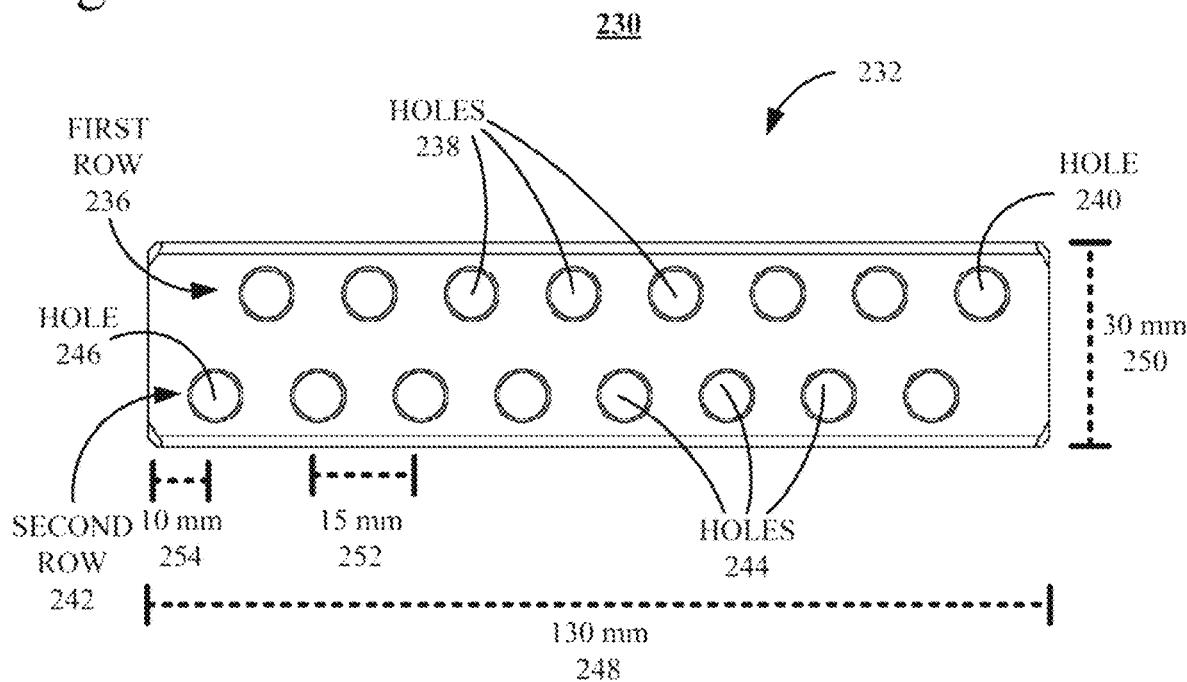
FIG. 5 is an illustration of one embodiment of a I Plate that may be employed in conjunction with the claimed subject matter.
Figure 5:
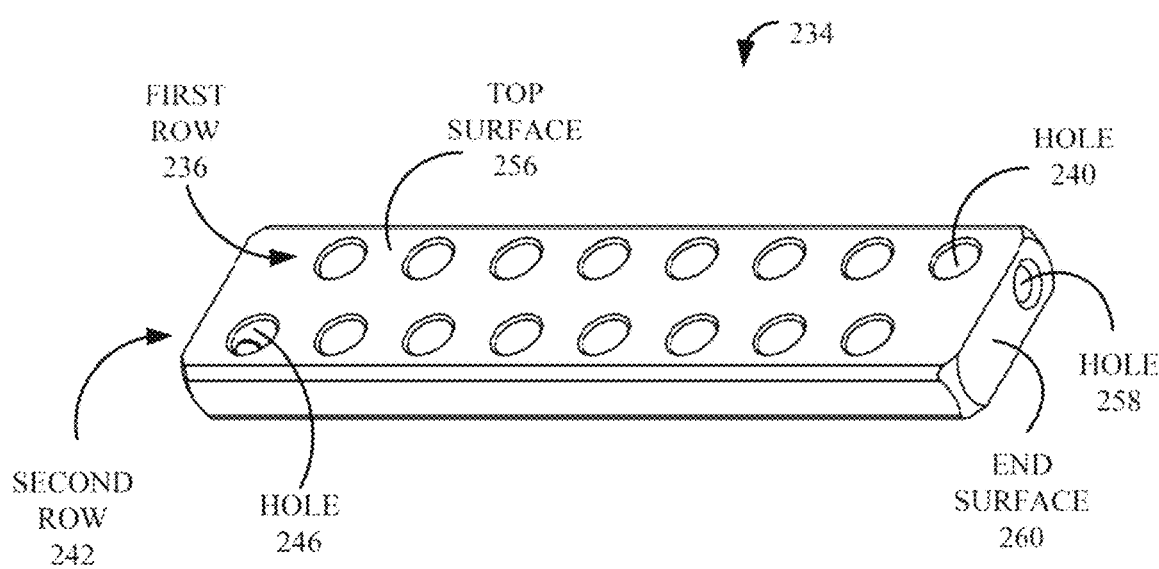

FIG. 5 is an illustration of two views of one embodiment of that which the Inventors have defined as an I Plate 230. I Plate 230 is illustrated from two (2) different angles, i.e., a top view 232 and a perspective view 234. I Plate 230 is typically employed to conform to a patient's foot or to extend portions of plates 100 (FIG. 1), 130 (FIG. 2), 160 (FIG. 3) and 200 (FIG. 4).

I Plate 230 includes a first row of holes 236, which includes holes 238 and an end hole 240, and a second row of holes 242, which includes holes 244 and an end hole 246. For the sake of simplicity, only four holes in each of rows 236 and 242 are labeled. In this example, I Plate 230 has a length 248 of one hundred thirty millimeters (130 mm), a width 250 of thirty millimeters (30 mm) and a thickness (not labeled) of ten millimeters (10 mm). Holes 238 and 244 in each row 236 and 242 are spaced a distance 252 of fifteen millimeters (15 mm) apart and end holes 240 and 246 are a distance 254 of ten millimeters (10 mm) from the respective edges of I plate 230. It should be noted that all holes in rows 236 and 242 extend through both a top surface 256 and a bottom surface (not shown) of I Plate 230.

An end surface 260 includes a hole 258 that is adjacent to the space between top surface 256 and the bottom surface that corresponds to hole 240. Although not shown, there is also a hole in the opposite end of I plate 230 that is adjacent to the space between top surface 256 and the bottom surface that corresponds to hole 246. Hole 258 and the hole in the opposite end of I Plate 230 are threaded and used to attach I Plate 230 to other components of the claimed subject matter.

Figure 6:
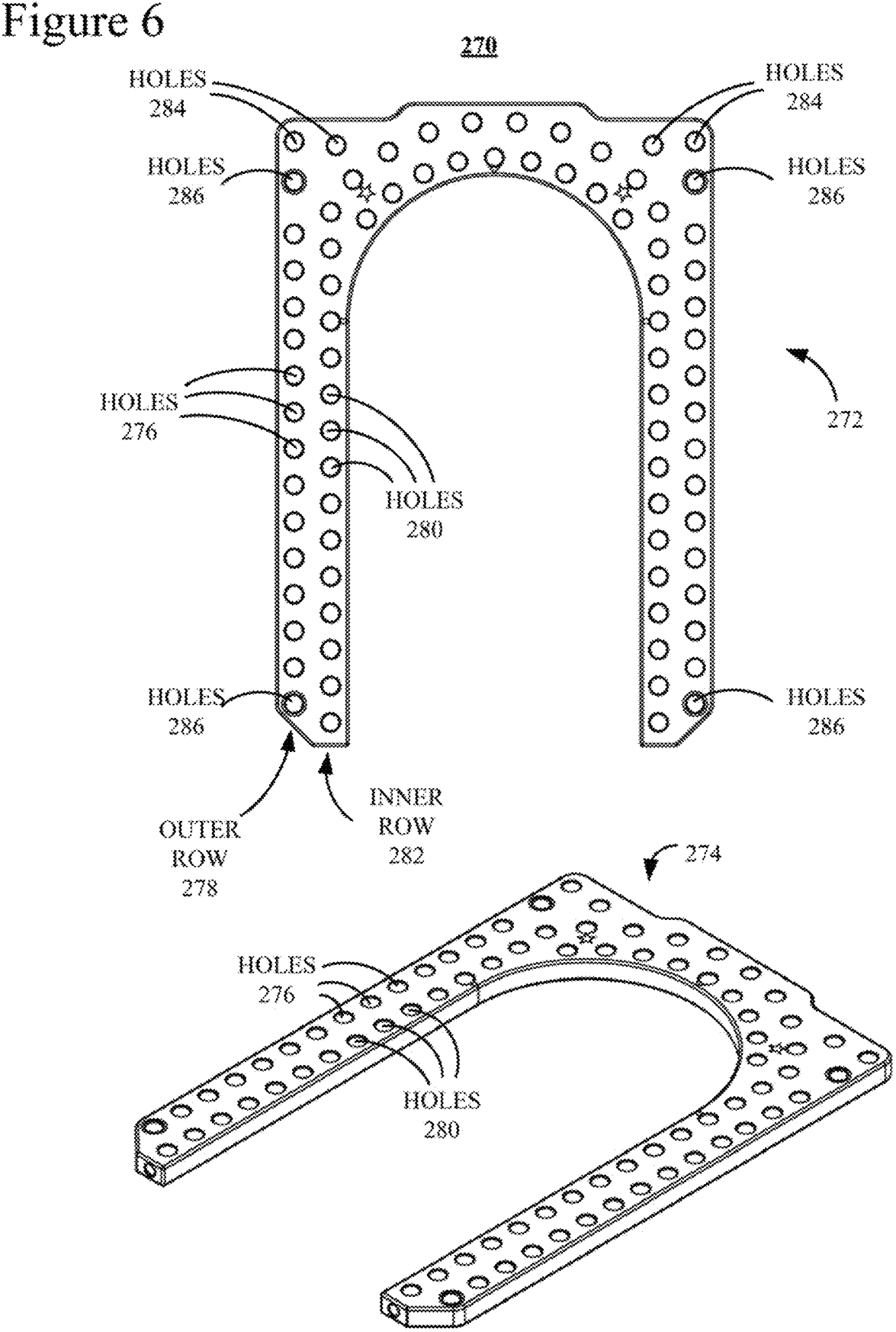
FIG. 6 is an illustration of one embodiment of Foot Plate that may be employed in conjunction with the claimed subject matter.

FIG. 6 is an illustration of two views of one embodiment of that which the Inventors have defined as a Foot Plate 270. Foot Plate 270 is illustrated from two (2) different angles, i.e., a top view 272 and a perspective view 274. Foot Plate 270 is typically employed to provide a platform for attachment to a customized combination of plates 100 (FIG. 1), 130 (FIG. 2), 160 (FIG. 3), 200 (FIG. 4) and 230 (FIG. 5). Like plates 100 130, 160, 200 and 230, Foot Plate 270 has holes 276 in an outer row 278 and holes 280 in an inner row 282. There are also extra holes 284 at corners of Foot Plate 260. Holes 284 merely provide extra points of attachment to Foot Plate 270. Four (4) holes 286 are provided for the attachment of "Rocker Rails," or "Walker Rails," (see 404, FIG. 9). Holes 276, 280 and 284 are spaced and positioned to align with the holes of plates 100, 130, 160, 200 and 230.

Figure 7:
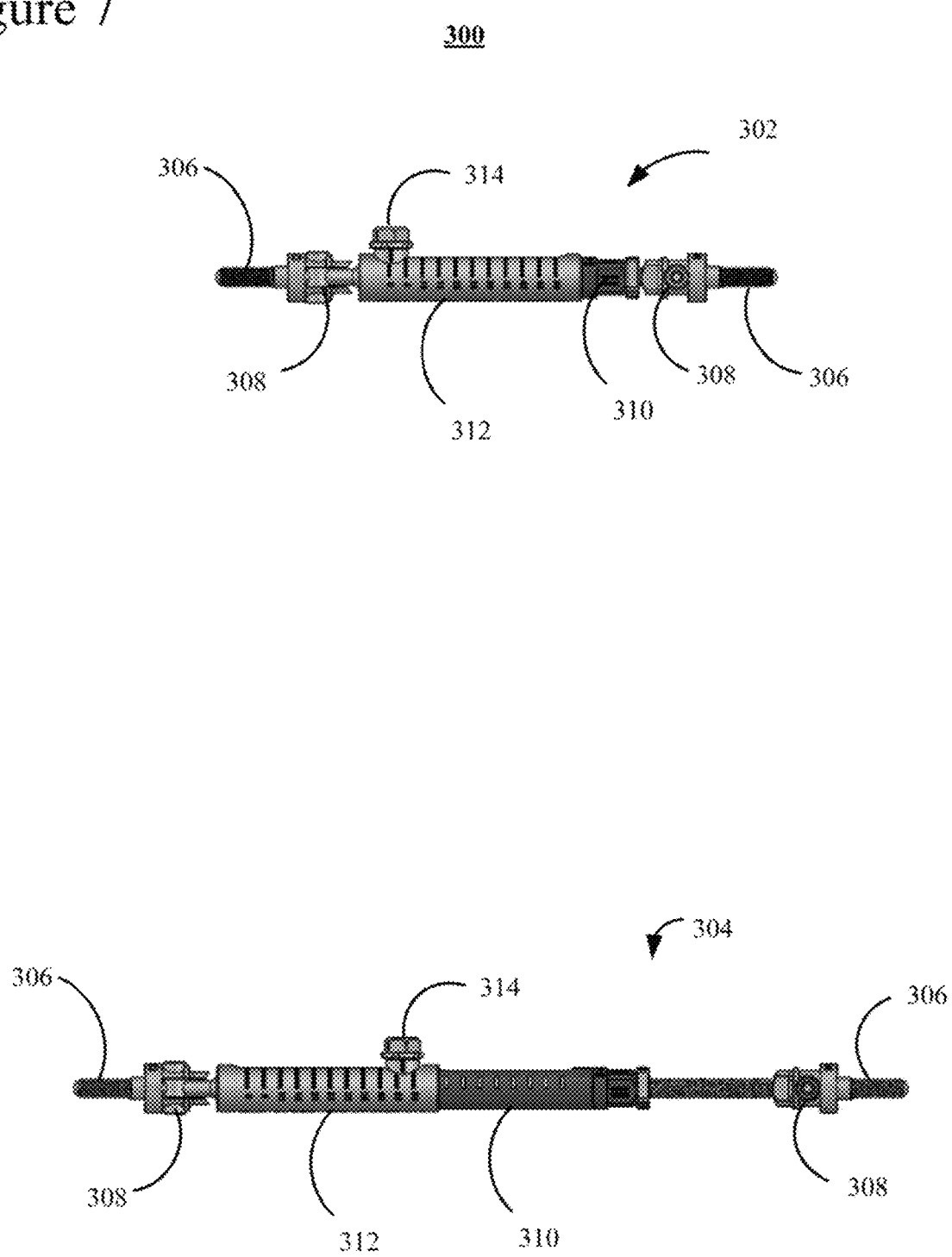
FIG. 7 is an adjustable strut that may be employed in conjunction with the claimed subject matter.

FIG. 7 is an illustration of an telescoping adjustable strut 300 that may be employed in conjunction with the claimed subject matter. Adjustable strut 300 is illustrated in two different configurations, i.e., a shortened configuration 302 and an extended position 304. It should be understood that adjustable strut 300 is adjustable to any length between a shortened configuration and a fully extended configuration. The example is of a "medium" length that may be shortened to as little as one hundred twenty-five millimeters (125 mm) and extended to a long as two hundred seven millimeters (207 mm).

Threaded rods 306 are attached to the ends of adjustable strut 300. Threaded rods 306 may be extended through holes of plates 100 (FIG. 1), 130 (FIG. 2), 160 (FIG. 3), 200 (FIG. 4), 230 (FIG. 5) and 270 (FIG. 6) and fixed with nuts (see 410, FIG. 9) to attach the various plates 100, 130, 160, 200, 230 and 270. Swivel joints 308 enable plates 100, 130, 160, 200, 230 and 270 to be coupled together in multiple configurations depending upon such factors as a patient's size and placement of the disclosed EBF system on a patient.

Adjustable strut 300 includes an inner sleeve 310 and an outer sleeve 312. Outer sleeve 312 fits over inner sleeve 310 and can be positioned to adjust the length of adjustable strut 300. A bolt 314 may be loosened to adjust the position of inner sleeve 310 and outer sleeve with respect to each other and tightened to secure a particular relative position.

Figure 8:
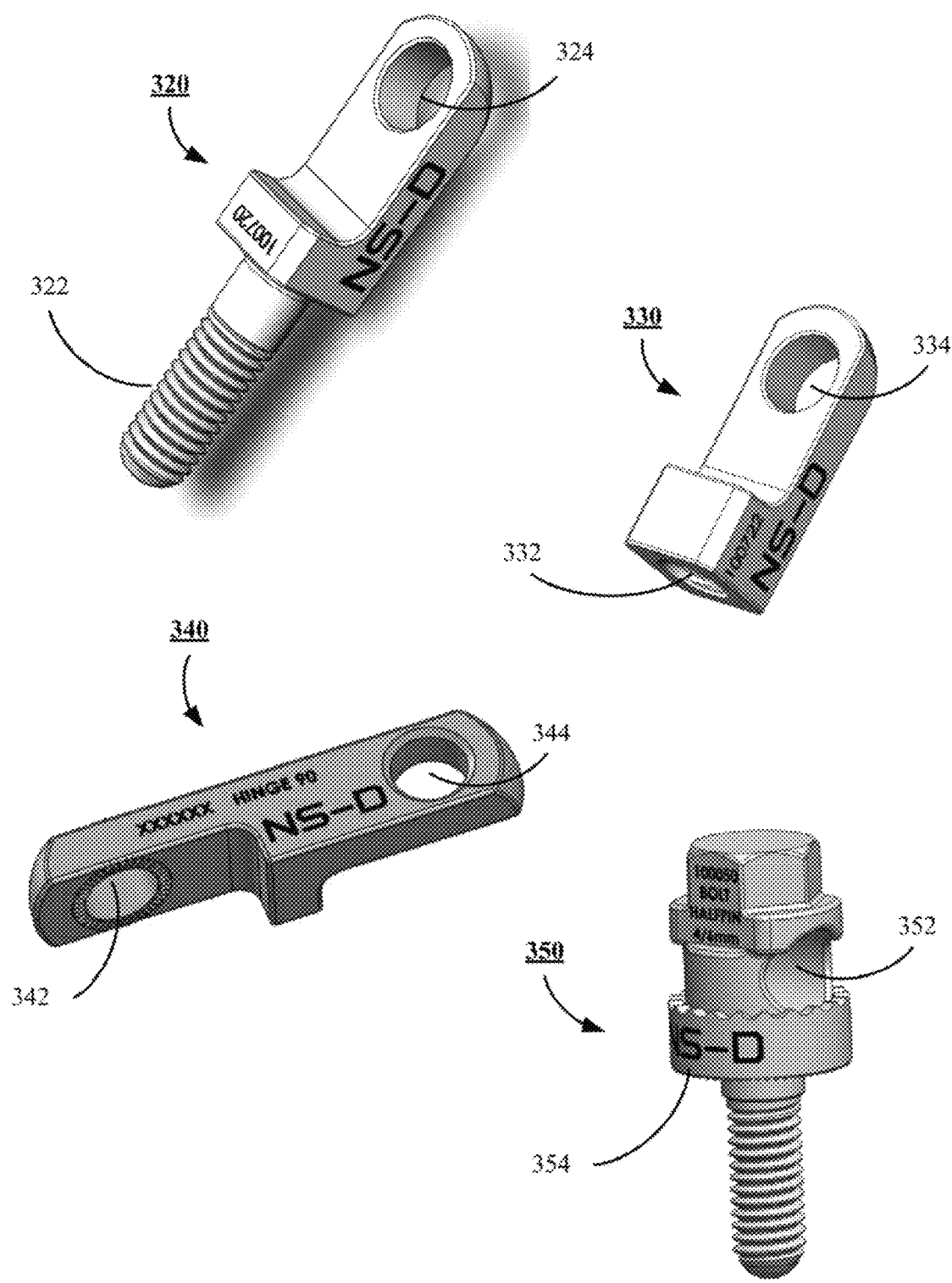
FIG. 8 is an illustration of three hinges and one bolt that may be employed in conjunction with an external bone fixation (EBF) system to affix the EBF system to a patient's extremity.

FIG. 8 is an illustration of three hinges and one bolt that may be employed in conjunction with an external bone fixation (EBF) system to affix the EBF system to a patient's extremity A male hinge 320 includes a threaded end 322 which is typically inserted through one of the holes of plates 100 (FIG. 1), 130 (FIG. 2), 160 (FIG. 3), 200 (FIG. 4), 230 (FIG. 5) and 270 (FIG. 6) and attached to the corresponding plates with a nut (not shown). A hole 324 provides an attachment point for a wire (see 504, FIG. 14), pin (see 506, FIG. 14) or other hardware to affix the EBF system to a patient's extremity or pelvis.

A female hinge 330 includes a threaded hole 332 that is used to attach hinge 330 to a plate such as plates 100, 130, 160, 200, 230 and 270. Typically, a bolt (not shown) would be inserted through one of the holes in the respective plate and threaded and tightened into hole 332. A hole 334 provides an attachment point for a wire, pin or other hardware to affix the EBF system to a patient's extremity or pelvis.

A ninety degree (90°) hinge 340 includes a threaded hole 342 that is used to attach hinge 340 to a plate such as plates 100, 130, 160, 200, 230 and 270. Typically a bolt (not shown) would be inserted through one of the holes in the respective plate and threaded and tightened into hole 342. A hole 344 provides an attachment point for a wire, pin or other hardware to affix the EBF system to a patient's extremity or pelvis.

A bolt 350 includes a hole 352 through which a pin (see 528, FIG. 15) or wire (see 530, FIG. 15) may be inserted. When bolt 350 is passed through a hole in one of plates 100, 130, 160, 200, 230 and 270 and a nut (not shown) is tightened, a collar 354 secures the pin or wire into hole 352.

Figure 9:
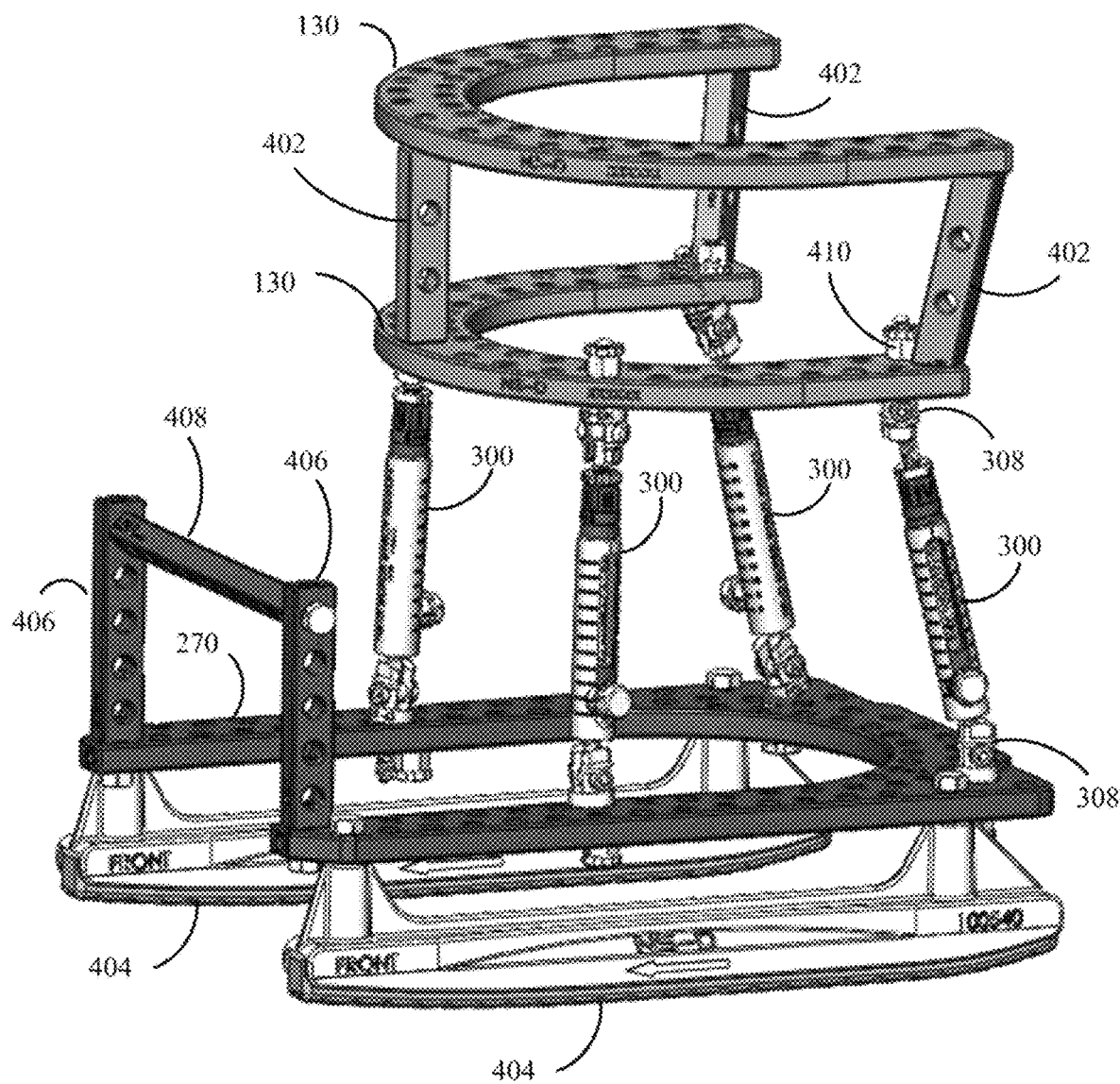
FIG. 9 is an illustration of a EBF system in accordance with the disclosed technology employing two N Plates in a welded "cascade" configuration, two posts with a Fore Foot Bridge, a Foot Plate and a pair of Walker Rails.

FIG. 9 is an illustration of one embodiment of an external fixation system (EFS) 400 in accordance with the disclosed technology that employs two N Plates 130 (FIG. 2), two posts 406 and Foot Plate 270 (FIG. 6). In a cascade configuration, N Plates 130 are affixed to each other with posts 402 that are welded or bolted in place. In addition, EBF system 400 includes two (2) Walker Rails 404. Walker Rails 404 may be attached to Foot Plate 270, providing a cushion or spring interface between EBF system 400 and the ground. In this example, N Plates 130 are coupled in a "cascade" configuration, which implies that N Plates 130 are permanently attached with posts 402 that have been welded or otherwise permanently affixed to N Plates 130. The lower N Plate 130 is coupled to Foot Plate 270 with adjustable struts 300 (FIG. 7). Posts 406 are attached to the front of Foot Plate 270 and Foot Plate 260 is attached to a pair of Walker Rails 404. Posts 406, which provide both stability to EBF system 400 and additional attachment points for wires (see 504, FIG. 13), pins (see 506, FIG. 13) and other hardware, may be stabilized by a Fore Foot Bridge 408.

Where employed, posts such as posts 402 may be either welded or otherwise permanently attached, i.e., in a pre-configured "cascade" configuration, or bolted, i.e., in a "stacked" configuration, to the respective components. Struts 300 are typically attached to the respective components with nuts such as a nut 410 and swivel joints 308 (FIG. 7). In this manner, the various components are able be adjusted into any of a variety of positions. In addition, struts 300 are typically configured to be adjustable with respect to the length so that struts 300 may be both adjusted for a particular patient and also periodically lengthened during treatment to promote bone growth.

Figure 10:
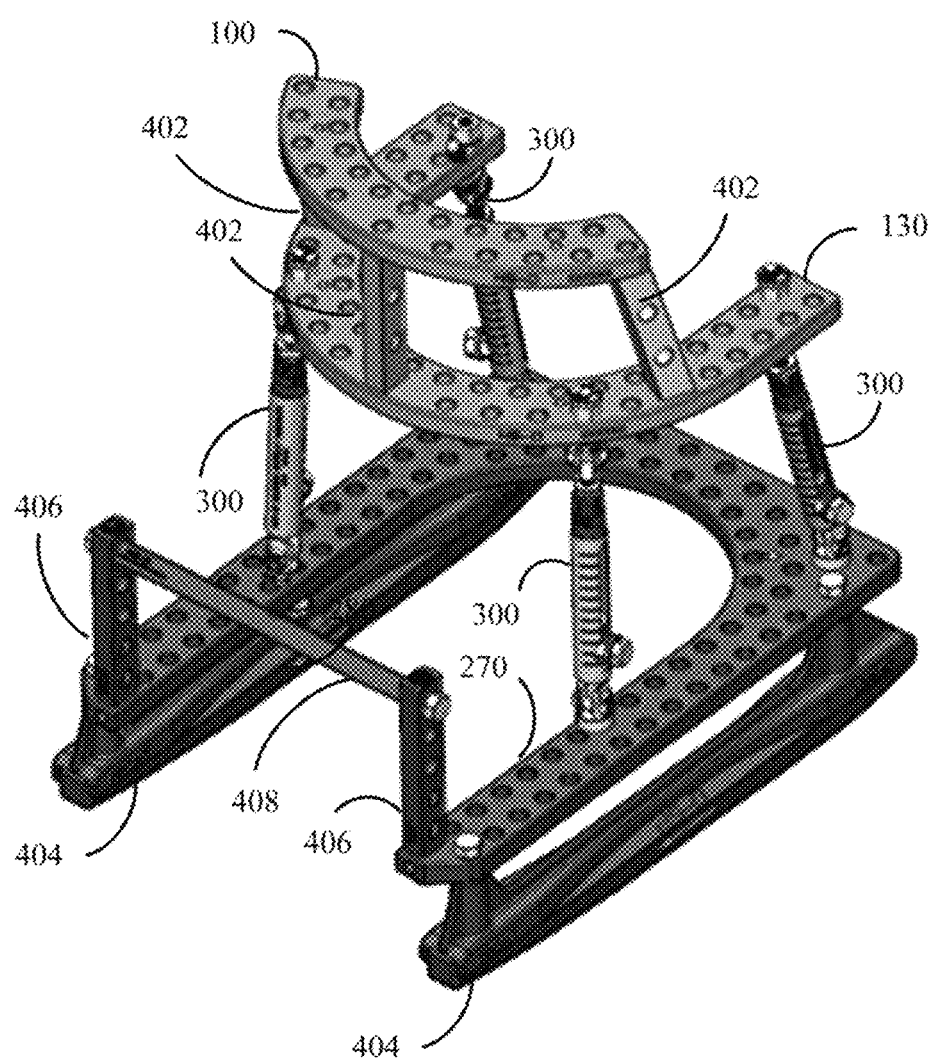
FIG. 10 is an illustration of one embodiment of an EBF system in accordance with the disclosed technology that employs a C Plate and an N Plate in a welded "stacked" configuration, a Foot Plate, two posts with a Fore Foot Bridge and a pair of Walker Rails.

FIG. 10 is an illustration of the one embodiment of an EBF system 420 in accordance with the disclosed technology that employs C Plate 100 (FIG. 1), N Plate 130 (FIG. 2), two posts 406 (FIG. 9), Foot Plate 270 (FIG. 6) and Fore Foot Bridge 408 (FIG. 9). C Plate 100 is coupled to the top N Plate 130 with posts 402 (FIG. 9) and N Plates 130 is attached to Foot Plate 270 (FIG. 6) with adjustable struts 300 (FIG. 7). In this example, C Plate 100 is affixed to N Plate 130 with posts 402, which are welded or bolted to C Plate 100 and N Plate 130 in a stacked configuration.

Like EBF system 400 (FIG. 9), Foot Plate 270 of EBF system 420 is attached to a pair of Walker Rails 404 (FIG. 9) and posts 406, which provide both stability to EBF system 420 and additional attachment points for wires (see 504, FIG. 14) and pins (see 506, FIG. 14) are coupled with Fore Foot Bridge 408 (FIG. 9).

Figure 11:
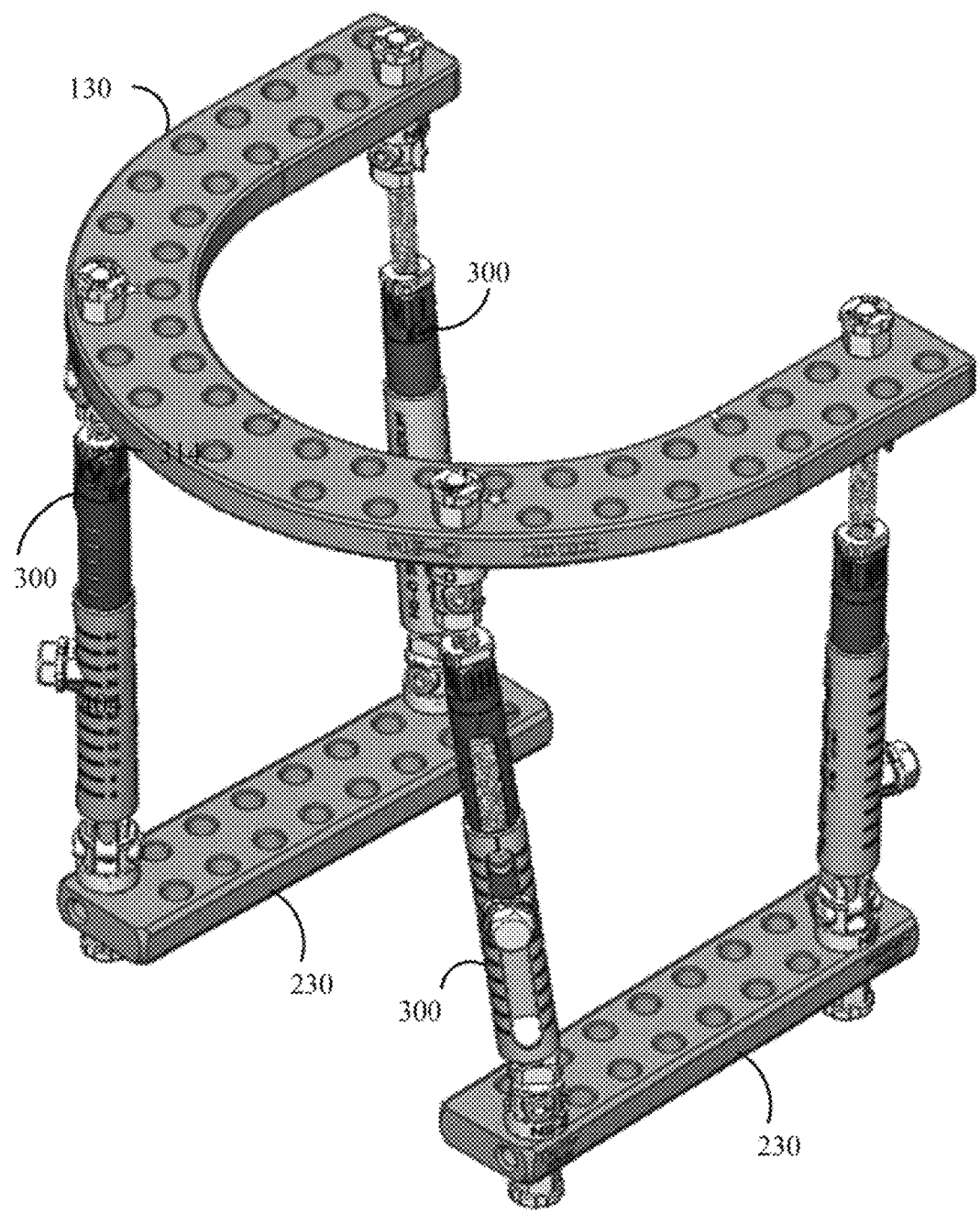
FIG. 11 is an illustration of one embodiment of an EBF system in accordance with the disclosed technology that employs an N Plate and two I Plates.

FIG. 11 is an illustration of one embodiment of an EBF system 440 in accordance with the disclosed technology that employs N Plate 130 (FIG. 2) and two I Plates 230 (FIG. 5). N Plate 130 is coupled to I Plates 230 with telescoping adjustable struts 300 (FIG. 7). This particular configuration may be employed, for example, to secure a patient's tibia (not shown) and foot (not shown) by attaching N Plate 130 to the tibia and I Plates 230 to the foot.

Figure 12:
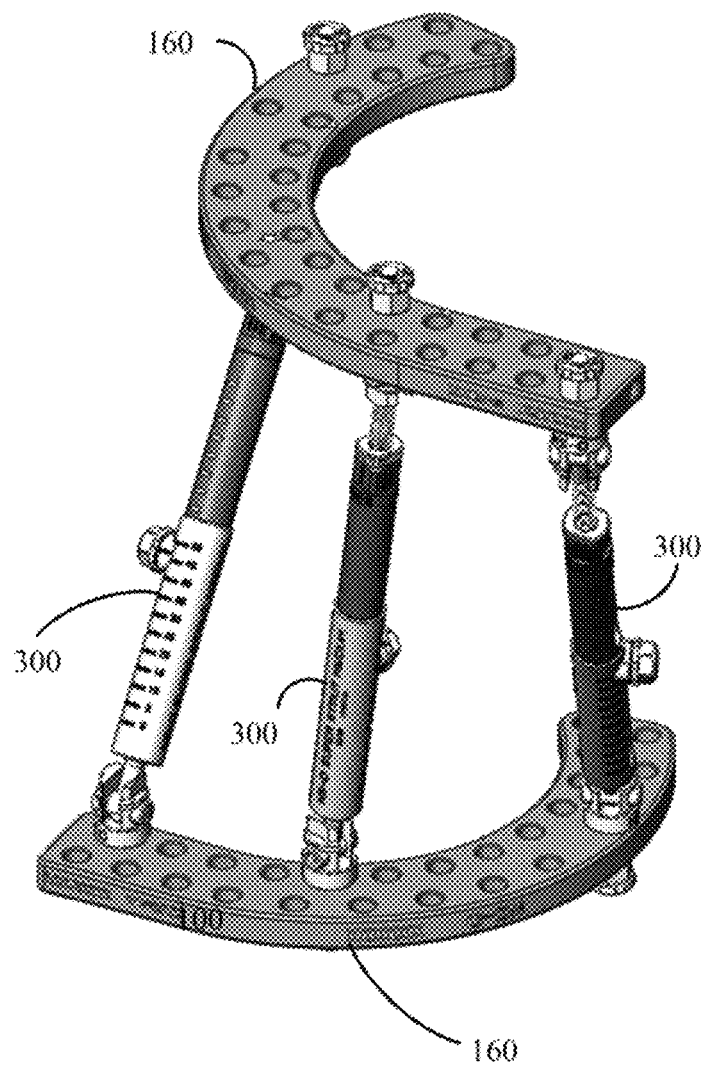
FIG. 12 is an illustration of one embodiment of an EBF system in accordance with the disclosed technology that employs two J Plates.

FIG. 12 is an illustration of one embodiment of an EBF system 460 in accordance with the disclosed technology that employs two J Plates 160 (FIG. 3). J Plates 160 are coupled with telescoping adjustable struts 300 (FIG. 7). Like EBF system 440 (see FIG. 11), this particular configuration may be employed, for example, to secure a patient's tibia (not shown) and foot (not shown) (see FIG. 15).

Figure 13:
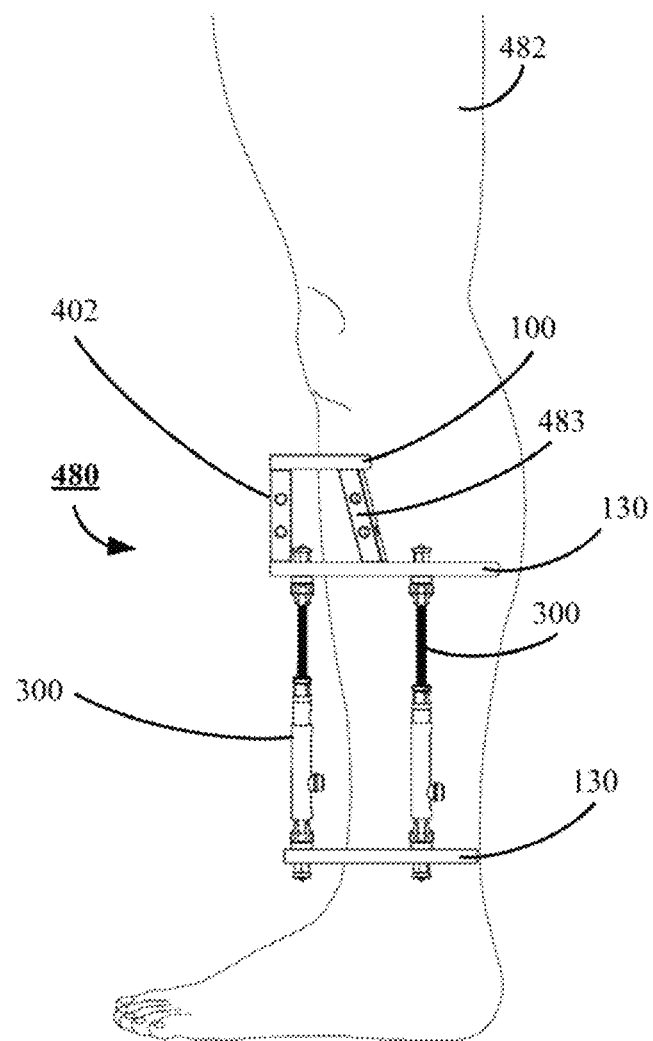
FIG. 13 is an illustration of the one embodiment of an EBF system in accordance with the disclosed technology that employs a C Plate and two N Plates, illustrated in conjunction with a patient's extremity under treatment.

FIG. 13 is an illustration of one embodiment of an EBF system 480 in accordance with the disclosed technology that employs one C Plate 100 (FIG. 1) and two N Plates 130 (FIG. 2), illustrated in conjunction with a patient's leg 482. C Plate 100 is coupled to upper N Plate 130 with post 402 (FIG. 9) and two angled posts 483, of which only one is visible in this drawing, Upper N Plate 130 is coupled with lower N Plate 130 with telescoping adjustable struts 300 (FIG. 7). EBF 480 would be affixed to a tibia of leg 482 with a combination of pins and/or wires, which are not shown in this drawing (see FIG. 15). It should be noted, that this particular configuration, unlike convention systems with circular rings, would enable the patient to lie on their back without being encumbered by EBF system 480.

Figure 14:
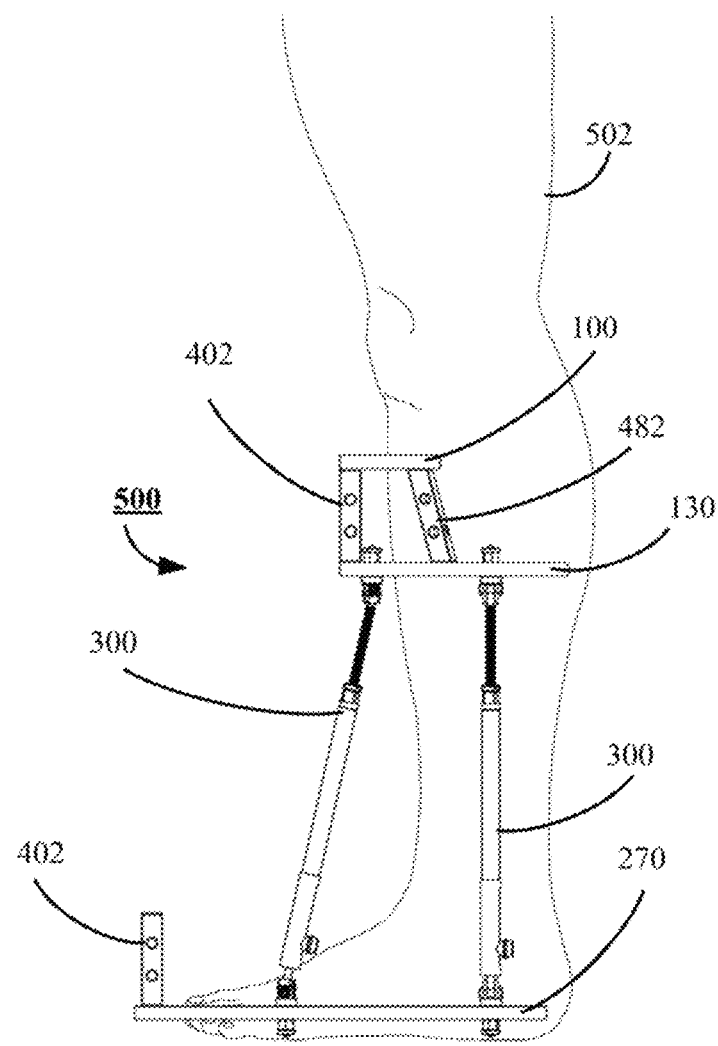
FIG. 14 is an illustration of the one embodiment of an EBF system in accordance with the disclosed technology that employs a C Plate, an N Plate, a Foot Plate and six posts, only three of which are visible, illustrated in conjunction with a patient's extremity under treatment.

FIG. 14 is an illustration of one embodiment of an EBF system 500 in accordance with the disclosed technology that employs C Plate 100 (FIG. 1), N Plate 130 (FIG. 2) and Foot Plate 270 (FIG. 6), illustrated in conjunction with a patient's leg 502. C Plate 100 is coupled to N Plate 130 with a post 402 (FIG. 9) and two angled posts 482 (see FIG. 13), of which only one is visible in this drawing, N Plate 130 is coupled to Foot Plate 270 with telescoping adjustable struts 300 (FIG. 7). Also coupled to Foot Plate 270 are two posts 402 of which only one is visible in this drawing. EBF 500 would typically be affixed to a tibia of leg 502 and the foot of the patient with a combination of pins and/or wires, which are not shown in this drawing (see FIG. 15). It should be noted, that this particular configuration, like EBF system 480 and unlike convention systems with circular rings, would enable the patient to lie on their back without being encumbered by EBF system 500.

Figure 15:
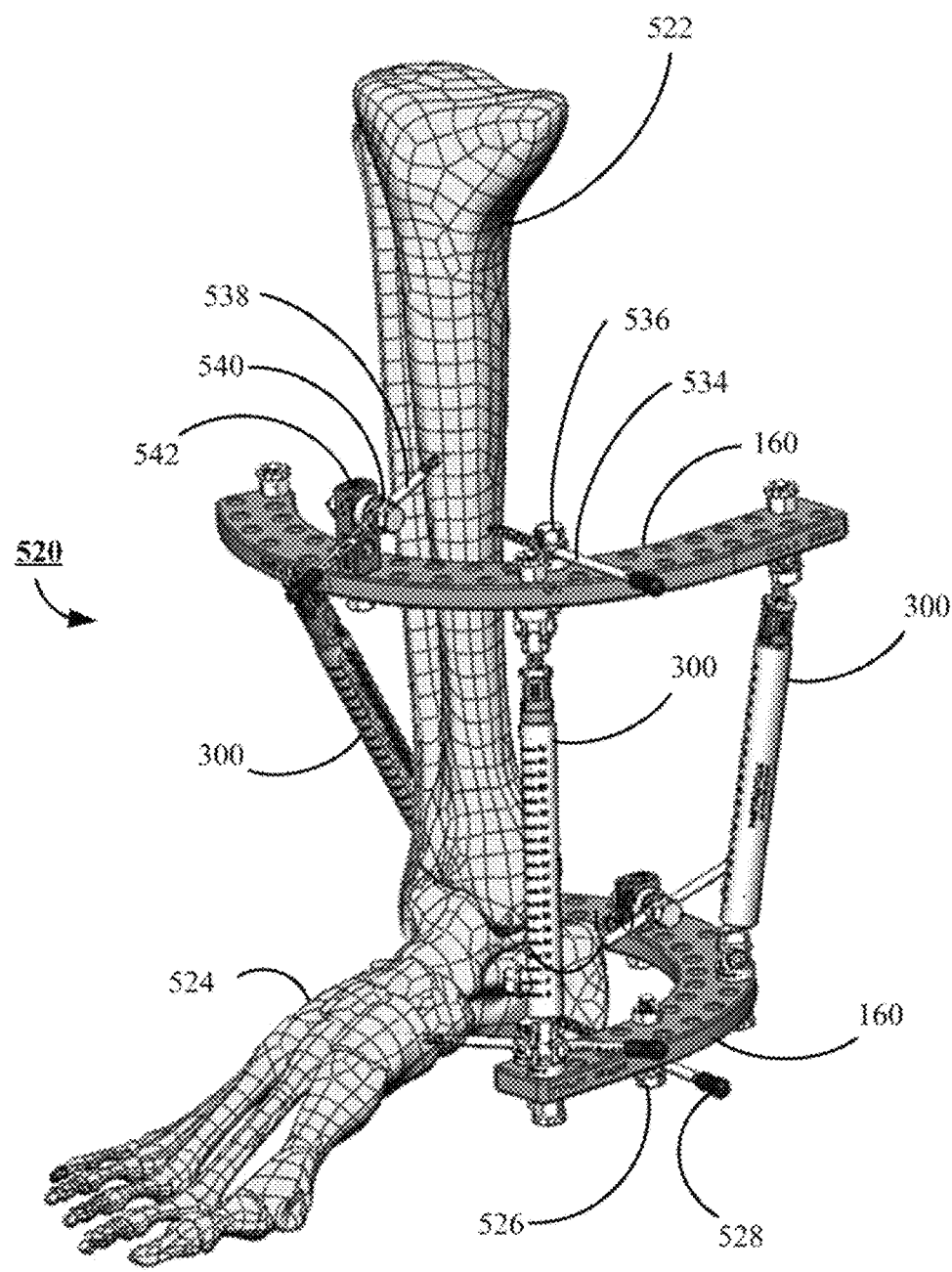
FIG. 15 is an illustration of an EBF system with two J Plates affixed to a patient's exposed tibia and foot.

FIG. 15 is an illustration of an EBF system 520 with two J Plates 160 (FIG. 3), illustrated affixed to a patient's exposed tibia 522 and foot bone 524. The patient's leg is not shown in this illustration. J Plates 160 are coupled with three telescoping adjustable struts 300 (FIG. 7). Attachments 526, such as hinges 320, 330 and 340 (FIG. 8) and bolt 350 (FIG. 8), are employed to attach half pins 528 to lower J Plate 160. In this figure bolt 350 is illustrated. For the sake of simplicity, only one attachment 526 and pin 528 are labeled. Half pins 528 are then attached to either a heel bone or foot bone 524. Upper J Plate 160 is affixed to tibia 522 with half pin 534 and attachment 536, which may be any of hinges 320, 330 and 340 (FIG. 8) and bolt 350 (FIG. 8). A second pin 538 is attached by means of a hinge 540 to a post 542 that is bolted to upper J Plate 160.

Figure 16:
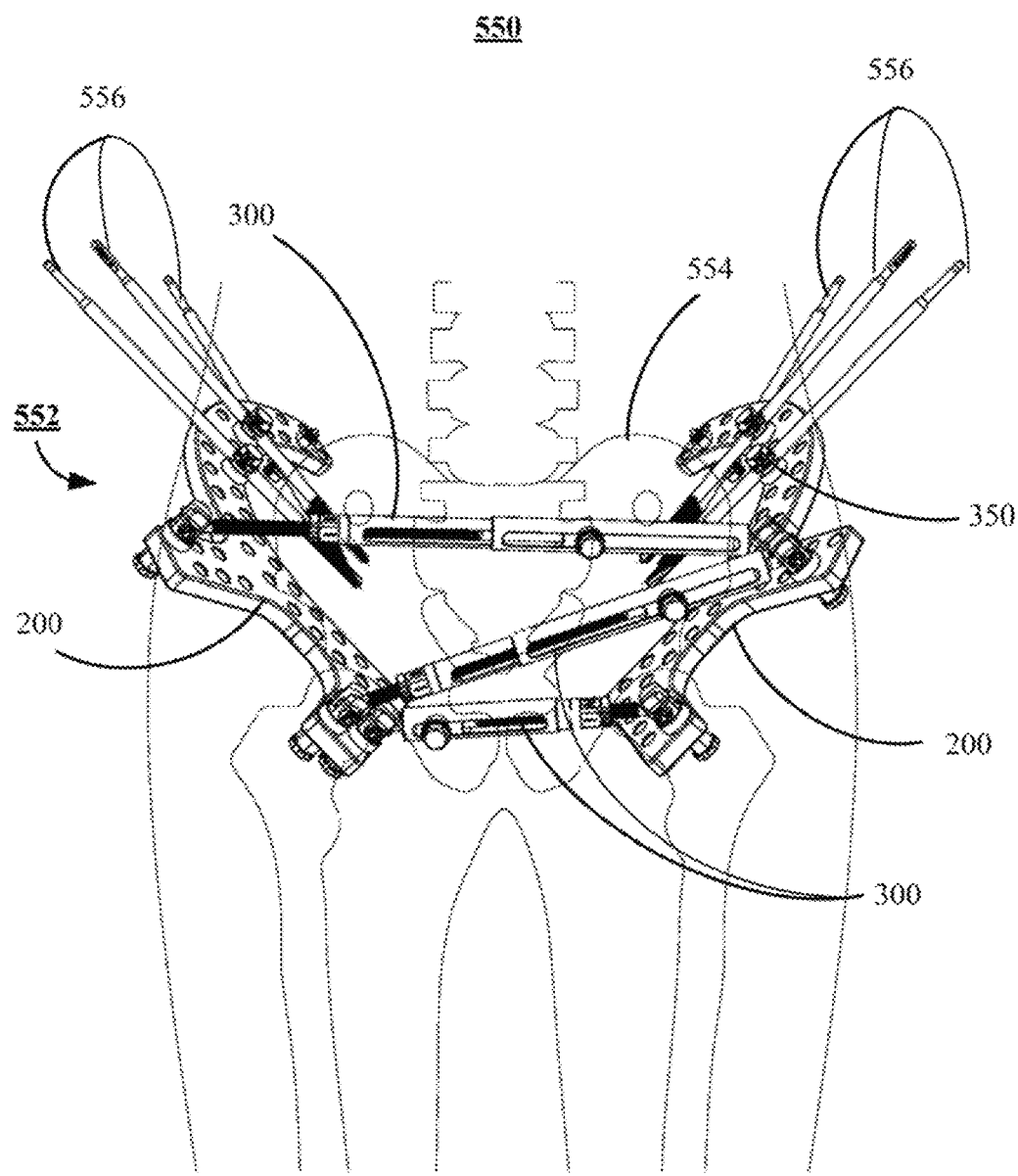
FIG. 16 is an illustration of one embodiment of an EBF system with two K Plates, illustrated in conjunction with a patient's pelvic bone under treatment.

FIG. 16 is an illustration of one embodiment of an EBF system 550 with two K Plates 200 (FIG. 4) from a front perspective 552, illustrated in conjunction with a patient's pelvic bone 554 under treatment. Plates 200, which may be bolted together, are coupled with three telescoping adjustable struts 300 (FIG. 7). The assembled system 550 is attached to pelvic bone 554 by means of pins 556. Pins 556 are coupled to K Plates 200 by means of hinges or bolts, which in this example is bolt 350 (FIG. 8), only one of which is labeled in FIG. 16 for the sake of simplicity.

Figure 17:
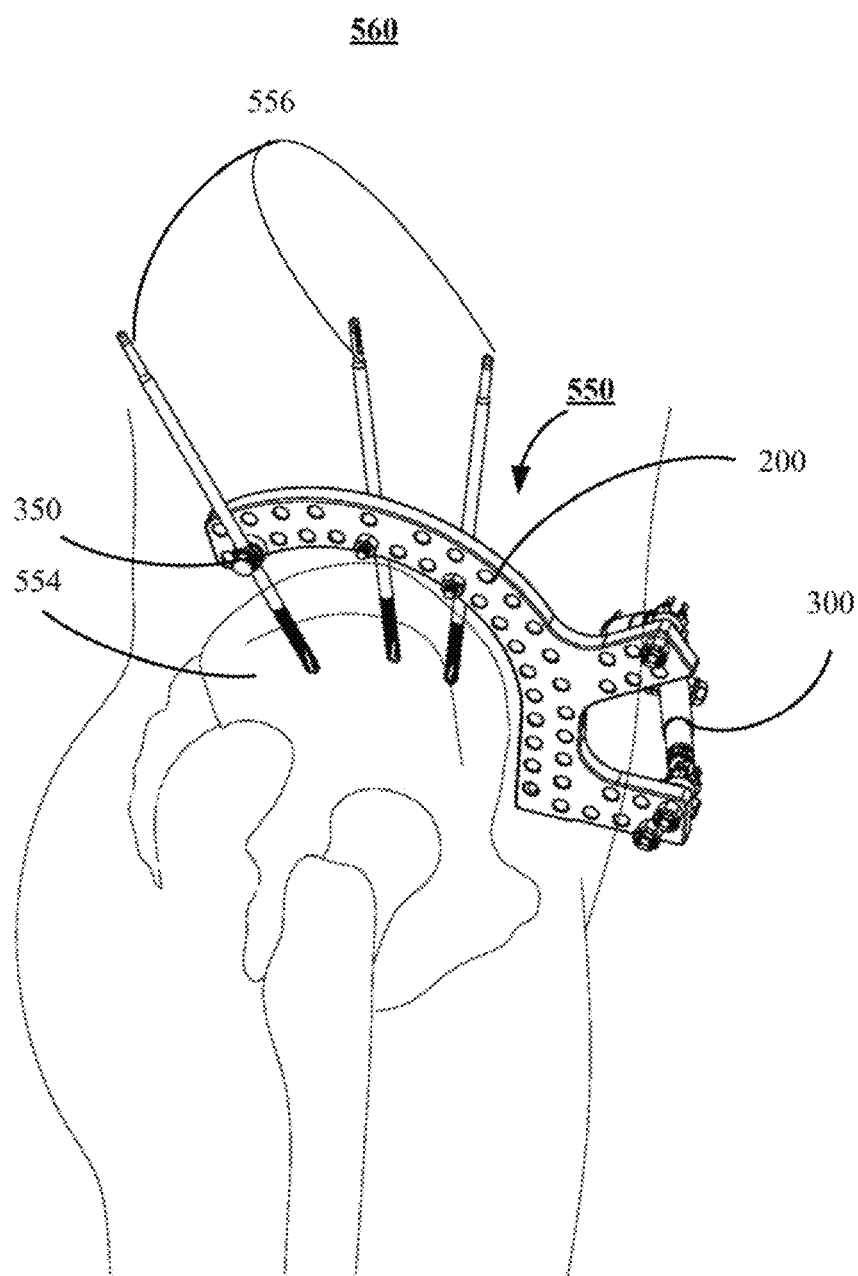
FIG. 17 is an illustration of the embodiment of the EBF system of FIG. 16 from a different perspective.

FIG. 17 is an illustration of the embodiment of EBF system 550 of FIG. 16 from a side perspective 560. Like perspective 552 of FIG. 16, perspective 560 includes pelvic bone 554, K Plate 200, telescoping adjustable strut 300, pins 556 and bolt 350.

It should be understood that the disclosed technology may be implemented in almost an infinite number of configurations depending upon the needs of any particular patient and HCP. A customized EBF device may be constructed based upon such factors as the size of a patient, the nature of an injury and a particular type of bone deformity that is in need of correction. In addition to the advantages of customization, the disclosed technology provides a patient with a more comfortable EBF device in that, unlike current EBF devices, the claimed subject matter provides a device does not need to surround a limb or torso under treatment, thereby enabling a patient to lie down unencumbered by the device.

Figure 18:
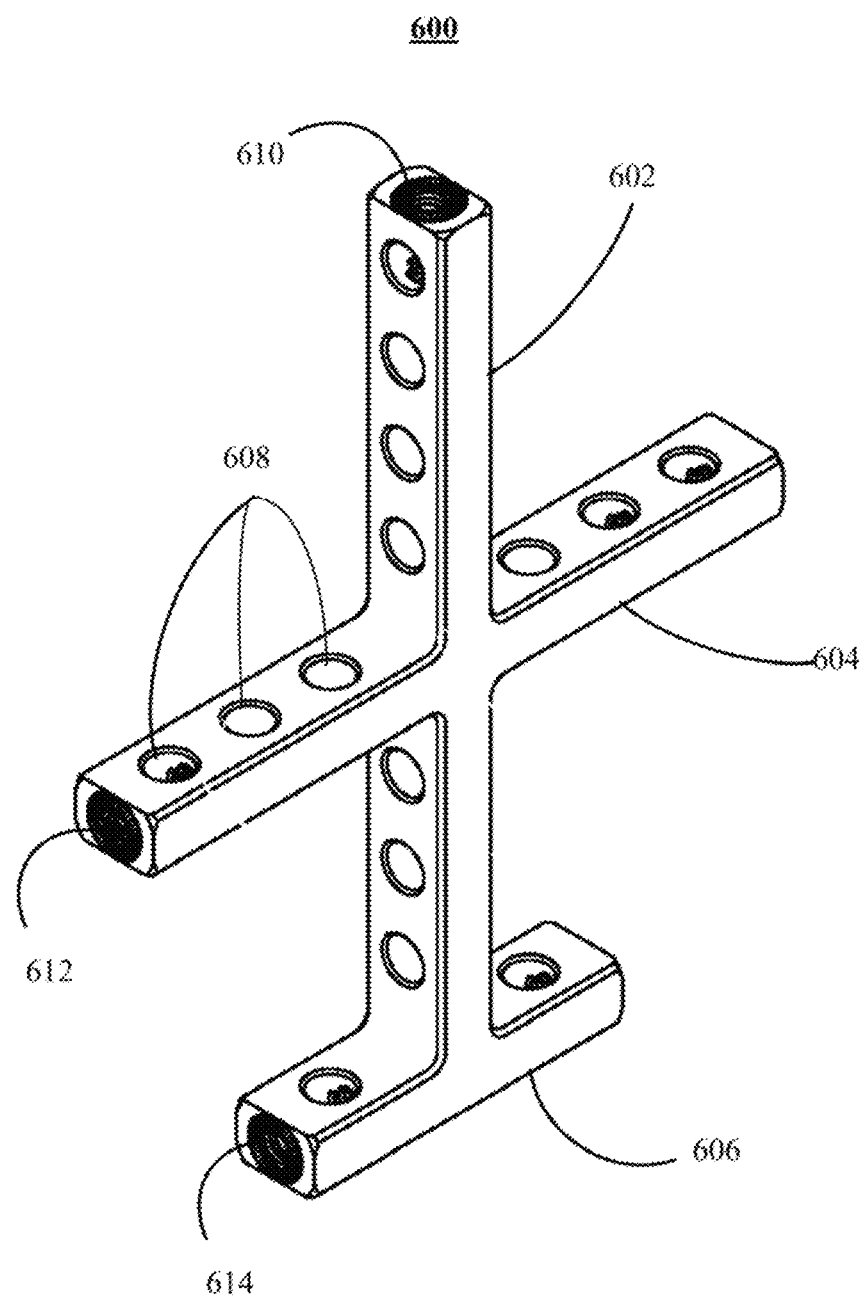
FIG. 18 is an illustration of one embodiment of a T Plate that may be employed in conjunction with the claimed subject matter.

FIG. 18 is an illustration of one embodiment of that which the Inventors have defined as a T Plate 600. T Plate 600 includes a main bar 602, a middle bar 604 and an end bar 606. Middle bar 604 is perpendicular to main bar 602 and approximately half way between one end of main bar 602 and end bar 606, which is also perpendicular to main bar 602 and parallel to middle bar 604. In one embodiment, middle bar 604 is welded to main bar 602 to form a '+' construct. End bar 606 may also be welded to main bar 602 or, in an alternative embodiment removably attached with a bolt or screw. T Plate may also be machined from a sheet of metal. In addition, other components such as C Plate 100 (FIG. 1) may be attached to main bar 602 rather than end bar 606. Although not illustrated, main bar 602 may include a notch to accommodate end bar 606 or another component such as C Plate 100.

All of bars 602, 604 and 606 include holes 608, which for the sake of only holes of middle bar 604 are labeled. It should be noted that all holes 608 in bars 602, 604 and 606 extend through the respective bars 602, 604 and 606. At ends of bars 602, 604 and 606 are threaded holes 610, 612 and 614, respectively. Although not visible in FIG. 18, each of bars 602, 604 and 606 also have threaded holes corresponding to threaded holes 610, 612 and 614, respectively, in the non-visible ends of bars 602, 604 and 606. Holes 608, 610, 612 and 614 used to attach T Plate 600 to other components of the claimed subject matter.

T Plate 600 may be employed to provide support to a patient's leg or other bone with main bar 602 in parallel to the leg bone and bars 602, 604, 606 and other components such as plates 100, 130 (FIG. 2), 160 (FIG. 3), 200 (FIG. 4), 230 (FIG. 5), 270 (FIG. 6) and struts 300 (FIG. 7) attached to the bone with pins 528 (FIG. 15) and wires 530 (FIG. 15).

Figure 19:
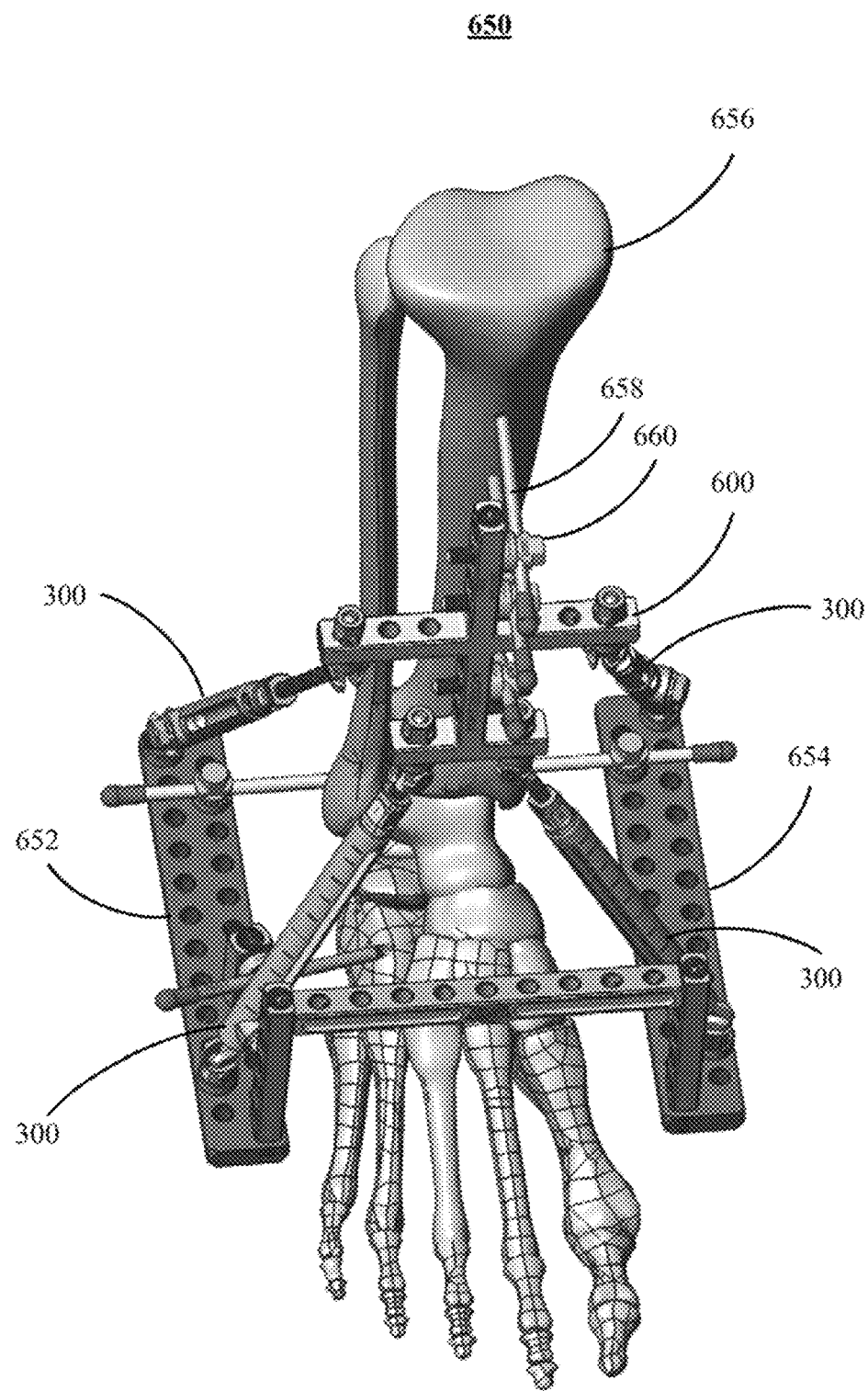
FIG. 19 is an illustration of one embodiment of an EBF system with a T Plate and two I Plates, illustrated in conjunction with a patient's tibia under treatment.

FIG. 19 is an illustration of one embodiment of an EBF system 650 with a T Plate 600 (FIG. 18) and two I Plates 652 and 654, illustrated in conjunction with a patient's tibia 656 under treatment. T Plate 600 is attached to I Plates 652 and 654 with four (4) adjustable struts 300 (FIG. 7). T Plate 600 is attached to tibia 656 by means of three (3) pins 658, only one of which is labeled, and attachments 660, only one of which is labeled and which may be any of hinges 320, 330 and 340 (FIG. 8) and bolt 350 (FIG. 8).

Figure 20:
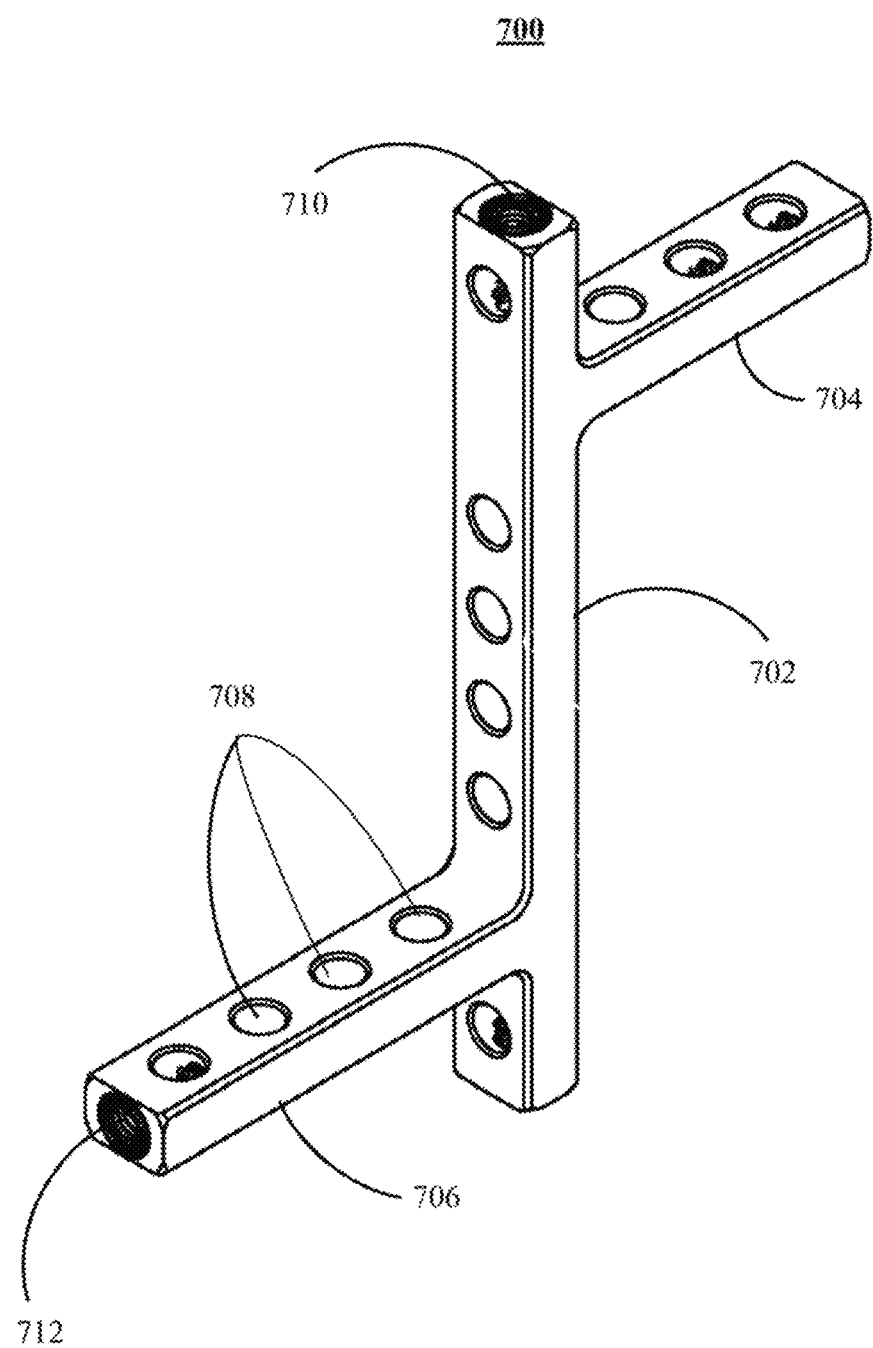
FIG. 20 is an illustration of one embodiment of a Z Plate that may be employed in conjunction with the claimed subject matter.

FIG. 20 is an illustration of one embodiment of that which the Inventors have defined as an Z Plate 700. Z Plate 700 includes a main bar 702 and two end bars 704 and 706. End bars 704 and 706 are perpendicular to main bar 702, parallel to each other and extend from main bar 702 close to opposite ends of main bar 7022. All of bars 702, 704 and 706 include holes 708, which for the sake of only holes of end bar 706 are labeled. It should be noted that all holes 708 in bars 702, 704 and 706 extend through the respective bars 702, 704 and 706. At ends of bars 702 and 706 are threaded holes 710 and 712, respectively. Although not visible in FIG. 19, main bar 702 and end bar 704 also have threaded holes corresponding to threaded holes 710 and 712, respectively, in the non-visible ends of bars 702 and 704. Holes 708, 710 and 712 used to attach Z Plate 700 to other components of the disclosed technology.

Like T Plate 600, Z Plate 700 may be employed to provide support to a patient's leg or other bone with main bar 702 in parallel to the leg bone and bars 704, 706 and other components such as plates 100, 130 (FIG. 2), 160 (FIG. 3), 200 (FIG. 4), 230 (FIG. 5), 270 (FIG. 6) and struts 300 (FIG. 7) attached to the bone with pins 528 (FIG. 15) and wires 530 (FIG. 15).

Figure 21:
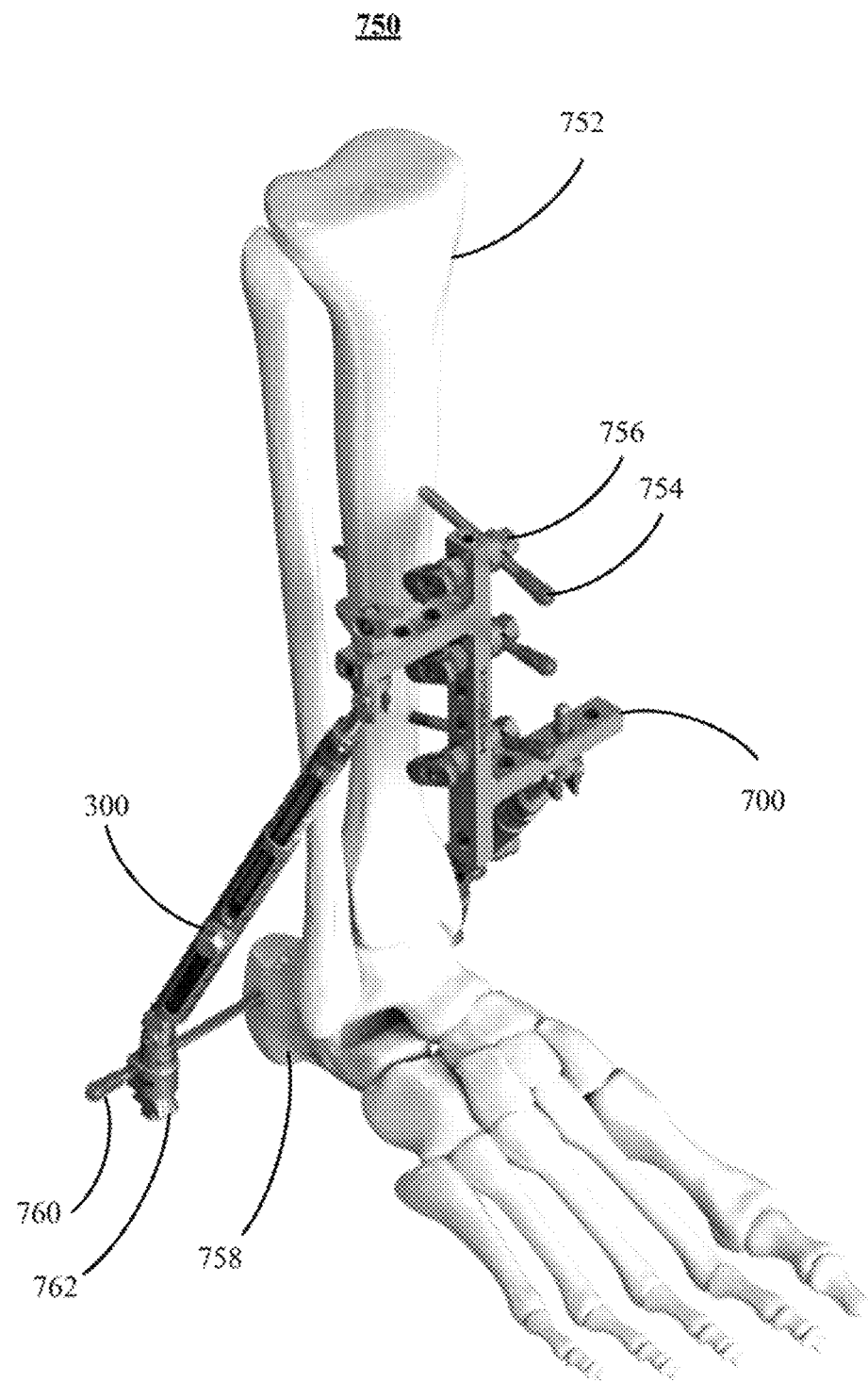
FIG. 21 is an illustration of one embodiment of an EBF system with a Z Plate, illustrated in conjunction with a patient's tibia under treatment.

FIG. 21 is an illustration of one embodiment of an EBF system 750 with a Z Plate 700 (FIG. 20), illustrated in conjunction with a patient's tibia 752 under treatment. Z Plate 700 is attached to tibia 752 by means of three (3) pins 754, only one of which is labeled, and attachments 756, only one of which is labeled and which may be any of hinges 320, 330 and 340 (FIG. 8) and bolt 350 (FIG. 8). Z Plate 700 is also attached to the patient's heel bond 758 with adjustable strut 300 (FIG. 7), a pin 760 and an attachment 762.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, elements, and/or components, but do not preclude the presence or addition of one or more other features, elements, components, and/or groups thereof. In addition the term "concave side" refers to the side of an arc on which a line drawn between any two points on the arc would lie. The term "convex side" refers to the side of an arc opposite the concave portion of the arc.

The corresponding structures, materials, acts, and equivalents of all means plus function elements in the claims below are intended to include any structure, material, or act for performing the function in combination with other claimed elements as specifically claimed. The description of the claimed subject matter has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

We claim:

1. An apparatus for the external fixation of bones, comprising:
   a plurality of two or more fixation plates, the two or more fixation plates selected from a list, the list comprising:
      a plurality of generally C-shaped Plates;
      a plurality of generally N-shaped Plates,
      a plurality of generally J-shaped Plates;
      a plurality of generally I-shaped Plates;
      a plurality of generally Z-shaped Plates; and
      a plurality of generally T-shaped Plates;
   a plurality of telescoping adjustable struts that connect a first fixation plate of the plurality of fixation plates with a second fixation plate of the plurality of fixation plates, wherein the first and second fixation plates are adjacent plates; and
   a plurality of posts, each post connecting two adjacent fixation plates of the plurality of fixation plates.

2. The apparatus of claim 1, the list further comprising a plurality of generally K-shaped Plates.

3. The apparatus of claim 1, the list further comprising a plurality of Foot Plates.

4. The apparatus of claim 3, further comprising:
   a plurality of posts coupled to the foot plate; and
   a plurality of bridges, each bridge coupled at an end to a corresponding post and couples at an opposite end to the second fixation plate.

5. The apparatus of claim 1, further comprising:
   a plurality of holes in each of the plurality of fixation plates; and
   a plurality of fixation devices selected from a fixation list, the fixation list comprising:
      a plurality of pins; and
      a plurality of wires;
   wherein each fixation device of the plurality of fixation devices is coupled to at least one hole of the plurality of holes and configured to secure a bone within the plurality of fixation plates.

6. The apparatus of claim 1, wherein at least two of the fixation plates and posts are in a cascade configuration.

7. The apparatus of claim 1, wherein at least two of the fixation plates and posts are welded together.

8. The apparatus of claim 1, wherein at least two of the fixation plates and posts are in a stacked configuration.

9. The apparatus of claim 1, each of the plurality of adjustable telescoping struts comprising a plurality of swivel hinges for attaching to the fixation plates.

10. A system for the assembly of a customized orthopedic external bone fixation device, comprising:
    a plurality of fixation plates, the plurality of fixation plates comprising:
       a plurality of generally C-shaped Plates;
       a plurality of generally N-shaped Plates;
       a plurality of generally J-shaped Plates,
       a plurality of generally I-shaped Plates;
       a plurality of generally Z-shaped Plates; and
       a plurality of generally T-shaped Plates;
    a plurality of coupling devices, the coupling device selected from a list, the list comprising:
       a plurality of adjustable telescoping struts; and
       a plurality of posts;
       wherein each of the coupling devices is configured to affix a first fixation plate of the plurality of fixation plates with a second fixation plate of the plurality of fixation plates; and
       wherein the first and second fixation plates are adjacent plates.

11. The system of claim 10, the fixation plates further comprising a plurality of generally K-shaped Plates.

12. The system of claim 10, the fixation plates further comprising a Foot Plate.

13. The system of claim 10, the plurality of fixation plates further comprising:
    a plurality of holes in each of the plurality of fixation plates; and
    a plurality of pins, each pin coupled to at least one hole of the plurality of holes, configures to secure a bone within the plurality of fixation plates.

14. The system of claim 13, wherein the plurality of holes in each fixation plate comprises a double row of holes.

15. The system of claim 10, further comprising:
    a plurality of pins; and
    a plurality of wires,
    wherein the pins and wires are for securing a bone within the plurality fixation plates.

16. The system of claim 10, each of the plurality of adjustable telescoping struts comprising a plurality of swivel hinges for attaching the struts to the fixation plates.

17. The apparatus of claim 10, wherein at least two of the fixation plates are in a stacked configuration.

18. The system of claim 10, wherein at least two of the fixation plates and posts are in a cascade configuration.

19. The system of claim 10, wherein at least two of the fixation plates are welded together.

* * * * *